US006080548A

United States Patent [19]
Au-Young et al.

[11] Patent Number: 6,080,548
[45] Date of Patent: Jun. 27, 2000

[54] CYCLIC NUCLEOTIDE PHOSPHODIESTERASES

[75] Inventors: Janice Au-Young, Berkeley; Benjamin G. Cocks, Palo Alto; Roger Coleman, Mountain View; Jeffrey J. Seilhamer, Los Altos; Douglas A. Fisher, Groton, all of Calif.

[73] Assignee: Incyte Pharmaceuticals, Inc., Palo Alto, Calif.

[21] Appl. No.: 09/255,748

[22] Filed: Feb. 23, 1999

Related U.S. Application Data

[62] Division of application No. 08/974,565, Nov. 19, 1997, Pat. No. 5,932,423.

[51] Int. Cl.$^7$ .............................. C07K 7/04; C07K 14/47
[52] U.S. Cl. ........................ 435/7.1; 530/300; 530/350; 435/4
[58] Field of Search .............................. 514/2; 530/350, 530/300, 324, 325, 326, 327, 328; 435/4, 7.1

[56] References Cited

PUBLICATIONS

Angel, J.B. et al., *Rolipram, a specific type IV phosphodiesterase inhibitor, is a potent inhibitor of HIV–1 replication*, AIDS (1995) 9:1137–1144.

Bang, Y.J. et al., *Terminal neuroendocrine differentiation of human prostate carcinoma cells in response to increased intracellular cyclic AMP*, Proc Natl Acad Sci USA (1994) 91:5330–5334.

Banner, K.H. and Page, C.P., *Immunomodulatory actions of xantines and isoenzyme selective phosphodiesterase inhibitors*, Mondaldi Arch Chest Dis (1995) 50:4,286–292.

Banner, K.H. and Page, C.P., *Theophylline and selective phosphodiesterase inhibitors as anti–inflammatory drugs in the treatment of bronchial asthma*, Eur Respir J (1995) 8:996–1000.

Beavo, Joseph A., *Cyclic Nucleotide Phosphodiesterase: Functional Implications of Multiple Isoforms*, Physiological Reviews (1995) 75:725–747.

Deonarain, M.P. and Epenetos, A.A., *Targeting enzymes for cancer therapy: old enzymes in new roles*, (1994) Br J Cancer 70:786–794.

Joulain, C. et al., *Influence of polyunsaturated fatty acids on lipid metabolism in human blood mononuclear cells and early biochemical events associated with lymphocyte activation*, J Lipid Mediators Cell Signalling (1995) 11:63–79.

Matousovic, K. et al., *Inhibitors of Cyclic Nucleotide Phosphodiesterase Isozymes Type–III and Type–IV Suppress Mitogenesis of Rat Mesangial Cells*, J Clin Invest (1995) 96:401–410.

Sasaki, H. et al., *Suppression of oro–facial movements by rolipram, a cAMP phosphodiesterase inhibitor, in rats chronically treated with haloperidol*, European Journal of Pharmacology (1995) 282:71–76.

Sommer, N., *The antidepressant rolipram suppresses cytokine production and prevents autoimmune encephalomyelitis*, Nature Medicine (1995) 1:244–248.

Thompson, W. J. *Cyclic Nucleotide Phosphodiesterases: Pharmacology, Biochemistry and Function*, Pharmac Ther (1991) 51:13–33.

Verghese, M.W. et al., *Regulation of Distinct Cyclic AMP–Specific Phosphodiesterase (Phosphodiesterase Type 4) Isozymes in Human Monocytic Cells*, Molecular Pharmacology (1995) 47:1164–1171.

Hillier, L., et al., *Zh47a11.r1 Soares fetal liver spleen 1NFLS S1 Homo sapiens cDNA clone 415196 5*, EST Accession No. W91922.

Bolger et al. (Jan. 1996) Alternative splicing of cAMP–specific phosphodiesterase mRNA transcripts. Characterization of a novel tissue–specific isoform, RNPDE4A8. J. Biol. Chem. 271:1065–1071.

*Primary Examiner*—Robert A. Schwartzman
*Attorney, Agent, or Firm*—Incyte Pharmaceuticals, Inc; Lynn E. Murry

[57] ABSTRACT

The invention provides human cyclic nucleotide phosphodiesterases (PDE8) and polynucleotides which identify and encode PDE8. The invention also provides expression vectors, host cells, antibodies, agonists, and antagonists. The invention also provides methods for treating or preventing disorders associated with expression of PDE8.

6 Claims, 32 Drawing Sheets

```
                9          18          27          36          45          54
5' NNC GAT ACT ATA AAT TCA TGC ATC AGG ATA GGC AAG GAG TGG CAA GGA ATT TAC 63          72          81          90          99         108
   TAT GCC AAA AAG AAA AAC GGA GAT AAT ATA CAA CAA AAT GTG AAG ATA ATA CCT 117         126         135         144         153         162
   GTC ATT GGA CAG GGA AAA ATT AGA CAC TAT GTG TCC ATT ATC AGA GTG TGC 171         180         189         198         207         216
   AAT GGC AAC AAT AAG GCT GAG AAA ATA TCC GAA TGT GTT CAG TCT GAC ACT CAT 225         234         243         252         261         270
   ACA GAT AAT CAG ACA GGC AAA CAT AAA GAC AGG AGA AAA GGC TCA CTA GAC GTC 279         288         297         306         315         324
   AAA GCT GTT GCC TCC CGT GCA ACT GAA GTT TCC AGC CAG AGA CAC TCT TCC 333         342         351         360         369         378
   ATG GCC CGG ATA CAT TCC ATG ACA ATT GAG GCG CCC ATC ACC AAG GTA ATC AAT
    M   A   R   I   H   S   M   T   I   E   A   P   I   T   K   V   I   N 387         396         405         414         423         432
   ATT ATC AAT GCT GCC CAG GAA AGT CCC ATG CCT GTG ACA GAA GCC CTA GAC
    I   I   N   A   A   Q   E   S   P   M   P   V   T   E   A   L   D
```

FIGURE 1A

```
      441          450          459          468          477          486
CGT GTG CTG GAA ATT CTA AGA ACC ACT GAG TTA TAT TCA CCA CAG TTT GGT GCT
 R   V   L   E   I   L   R   T   T   E   L   Y   S   P   Q   F   G   A 495          504          513          522          531          540
AAA GAT GAT GAT CCC CAT GCC AAT GAC CTT GTT GGG GGC TTA ATG TCT GAT GGT
 K   D   D   D   P   H   A   N   D   L   V   G   G   L   M   S   D   G 549          558          567          576          585          594
TTG CGA AGA CTA TCA GGG AAT GAA TAT GTT CTT TCA ACA AAA AAC ACT CAA ATG
 L   R   R   L   S   G   N   E   Y   V   L   S   T   K   N   T   Q   M 603          612          621          630          639          648
GTT TCA AGC AAT ATA ATC ACT CCC CTT GAT GAT GTC CCA CCA CGG ATA
 V   S   S   N   I   I   T   P   L   D   D   V   P   P   R   I 657          666          675          684          693          702
GCT CGG GCC ATG GAA AAT GAG GAA TAC TGG GAC TTT GAT ATT TTT GAA CTG GAG
 A   R   A   M   E   N   E   E   Y   W   D   F   D   I   F   E   L   E 711          720          729          738          747          756
GTT GCC ACC CAC AAT AGG CCT TTG ATT TAT CTT GGT CTC AAA ATG TTT GCT CGC
 V   A   T   H   N   R   P   L   I   Y   L   G   L   K   M   F   A   R 765          774          783          792          801          810
TTT GGA ATC TGT GAA TTC TTA CAC TGC TCC GAG TCA ACG CTA AGA TCA TGG TTA
 F   G   I   C   E   F   L   H   C   S   E   S   T   L   R   S   W   L
```

FIGURE 1B

```
      819               828               837               846               855               864
CAA ATT ATC GAA GCC AAT TAT CAT TCC TCC AAT TAC CAC AAT TCT ACA CAT
 Q   I   I   E   A   N   Y   H   S   S   N   Y   H   N   S   T   H 873               882               891               900               909               918
TCT GCT GAT GTG CTT CAT GCC ACT GCC TAT TTT CTC TCC AAG GAG AGG ATA AAG
 S   A   D   V   L   H   A   T   A   Y   F   L   S   K   E   R   I   K 927               936               945               954               963               972
GAA ACT TTA GAT CCA ATT GAT GAG GTC GCT GCA CTC ATC GCA GCC ACC ATT CAT
 E   T   L   D   P   I   D   E   V   A   A   L   I   A   A   T   I   H 981               990               999              1008              1017              1026
GAT GTG GAT CAC CCT GGG AGA ACC AAC TCC TTC CTG TGT AAT GCT GGA AGT GAG
 D   V   D   H   P   G   R   T   N   S   F   L   C   N   A   G   S   E 1035              1044              1053              1062              1071              1080
CTG GCC ATT TTG TAC AAT GAC ACT GCT GTG CTG GAG AGC CAC CAT GCG GCC TTG
 L   A   I   L   Y   N   D   T   A   V   L   E   S   H   H   A   A   L 1089              1098              1107              1116              1125              1134
GCC TTC CAG CTG ACC GGA GAT GAT AAA TGC AAT ATA TTT AAA AAC ATG GAG
 A   F   Q   L   T   G   D   D   K   C   N   I   F   K   N   M   E 1143              1152              1161              1170              1179              1188
AGG AAT GAT TAT CGG ACA CTG CGC CAG GGG ATT ATC GAC ATG GTC TTA GCC ACA
 R   N   D   Y   R   T   L   R   Q   G   I   I   D   M   V   L   A   T
```

FIGURE 1C

```
      1197        1206        1215        1224        1233        1242
GAA ATG ACA AGG CAC TTT GAG CAT GTC AAC AAA TTT GTC AAC AGC ATC AAC AAA
 E   M   T   R   H   F   E   H   V   N   K   F   V   N   S   I   N   K 1251        1260        1269        1278        1287        1296
CCC TTG GCA ACA CTA GAA GAA AAT GGG GAA ACT GAT AAA AAC CAG GAA GTG ATA
 P   L   A   T   L   E   E   N   G   E   T   D   K   N   Q   E   V   I 1305        1314        1323        1332        1341        1350
AAC ACT ATG CTT AGG ACT CCA GAG AAC CGG ACC CTA ATC AAA CGA ATG CTG ATT
 N   T   M   L   R   T   P   E   N   R   T   L   I   K   R   M   L   I 1359        1368        1377        1386        1395        1404
AAA TGT GCT GAT GTG TCC AAT CCC TGC CGA CCC CTG CAG TAC TGC ATC GAG TGG
 K   C   A   D   V   S   N   P   C   R   P   L   Q   Y   C   I   E   W 1413        1422        1431        1440        1449        1458
GCT GCA CGC ATT TCG GAA GAA TAT TTT TCT CAG ACT GAT GAA GAG AAG CAG CAG
 A   A   R   I   S   E   E   Y   F   S   Q   T   D   E   E   K   Q   Q 1467        1476        1485        1494        1503        1512
GGC TTA CCT GTG GTG ATG CCA GTG TTT GAC AGA AAT ACC TGC AGC ATC CCC AAA
 G   L   P   V   V   M   P   V   F   D   R   N   T   C   S   I   P   K 1521        1530        1539        1548        1557        1566
TCC CAA ATC TCT TTC ATT GAT TAC TTC ATC ACA GAC ATG TTT GAT GCT TGG GAT
 S   Q   I   S   F   I   D   Y   F   I   T   D   M   F   D   A   W   D
```

FIGURE 1D

```
       1575            1584            1593           1602           1611           1620
GCC TTT GTA GAC CTG CCT GAT TTA ATG CAG CAT CTT GAC AAC AAC TTT AAA TAC
 A   F   V   D   L   P   D   L   M   Q   H   L   D   N   N   F   K   Y 1629            1638            1647           1656           1665           1674
TGG AAA GGA CTG GAC GAA ATG AAG CTG CGG AAC CTC CGA CCA CCT CCT GAA TAG
 W   K   G   L   D   E   M   K   L   R   N   L   R   P   P   P   E   *

1683            1692            1701           1710           1719           1728
TGG GAG ACA CCA CCC AGA GCC CTG AAG CTT TGT TCC TTC CAT TTG GAA TTC 1737            1746            1755           1764           1773           1782
CTG AGG GCA RAC CAG AGC TCC TTG GTC CTT TCA GTR CWA GGC AGN ANA CAG CCC 1791            1800            1809           1818           1827           1836
CCG ATC TGY ATA GCC TGT GAA AGC CCR CGG GGA CAT CAG TAA CCT TCT KCA GCC 1845            1854            1863           1872           1881           1890
ACC ATC CAA TGC CAT TAC TGT CAA GTG AGA CTT GGC CMC TGT ARC CTG GGC CTK 1899            1908            1917           1926           1935           1944
CTK CAG GAG CTC TTC AGA AAG GCA CAT KAG GAC CAC GGN TTT SGC TCA GTT TCT
```

FIGURE 1E

```
              1953              1962              1971              1980              1989              1998
       GGT AAA ACA CAA GGT CTG GAG TKC CCC TGC MAA GGG TAT TGA TGG ACT TCC TKC 2007              2016              2025              2034              2043              2052
       CAG TGA CAG AGC ATG TCT ATT TCC AAC AAT TCT CTC ANT TAC GTT CAA CAC TTA 2061              2070              2079              2088              2097              2106
       AGA ACG GCT AAT GGC AAT AGG ATC TTT AAC AAC TTT TTC ACA TCA NAG NAG GTT 2115              2124              2133              2142              2151              2160
       CAA TCG CTC ACT TGG GNA CAC NAC TGA GAG TGA CTT CTC TTT TAA AAT TGA GTA 2169              2178              2187              2196
       ACA GAT GGA AAA ATA AAA TTT GGA CTT GAT TAT TAA NAT CCC N 3'
```

FIGURE 1F

```
                 9              18              27              36              45              54
5' NNC ATC AAC AAG CCA ATG GCA GCT GAG ATT GAA GGC AGC GAC TGT GAA TGC AAC
   X   I   N   K   P   M   A   A   E   I   E   G   S   D   C   E   C   N 63              72              81              90              99             108
   CCT GCT GGG AAG AAC TTC CCT GNA AAC CAA ATC CTG ATC AAA NGC ATG ATG ATT
   P   A   G   K   N   F   P   X   N   Q   I   L   I   K   X   M   M   I 117             126             135             144             153             162
   AAG TGT GCT GAN GNG GNC AAC CCA TGC CGA CCC TTG GAC CTG TGC ATT GAA TGG
   K   C   A   X   X   X   N   P   C   R   P   L   D   L   C   I   E   W 171             180             189             198             207             216
   GCT GGG AGG ATC TCT GAG GAG TAT TTT GCA CAG ACT GAT GAA GAG AAG AGA CAG
   A   G   R   I   S   E   E   Y   F   A   Q   T   D   E   E   K   R   Q 225             234             243
   GGA CTA CCT GTG GTG ATG NCA GTG TTT GAC C 3'
   G   L   P   V   V   M   X   V   F   D
```

FIGURE 2

```
                                9                18            27            36            45            54
5' CTT GCC TGT TTC CTG GAC AAA CAT CAT GAC ATT ATC ATA GAC CAC AGA AAT
   L   A   C   F   L   D   K   H   H   D   I   I   I   D   H   R   N 63            72            81            90            99           108
   CCT CGA CAG CTG GAT GCA GAG GCA CTG TGC AGG TCT ATC AGA TCA AAA CTC
   P   R   Q   L   D   A   E   A   L   C   R   S   I   R   S   K   L 117           126           135           144           153           162
   TCA GAA AAC ACA GTT ATT GTT GGT GTA CGC AGG GTG GAT AGA GAA GAG TTG
   S   E   N   T   V   I   V   G   V   R   R   V   D   R   E   E   L 171           180           189           198           207           216
   TCC GTA ATG CCT TTC ATT TCT GCT GGA TTT ACA CTG CTC CAG GAG TTT CCC
   S   V   M   P   F   I   S   A   G   F   T   L   L   Q   E   F   P 225           234           243           252           261           270
   AAC ATC ATG GCC TGC TAC AAT GAA CTG CTC CAG CTG GAG TTT GGA GAG GTG CGA
   N   I   M   A   C   Y   N   E   L   L   Q   L   E   F   G   E   V   R 279           288           297           306           315           324
   TCA CAA CTG AAA CTC AGG GCT TGT AAC TCA GTA TTC ACT GCA TTA GAA AAC AGT
   S   Q   L   K   L   R   A   C   N   S   V   F   T   A   L   E   N   S 333           342           351           360           369           378
   GAA GAT GCA ATT GAA ATT ACA AGC GAA GAC CGT TTT ATA CAG TAT GCA AAT CCT
   E   D   A   I   E   I   T   S   E   D   R   F   I   Q   Y   A   N   P
```

FIGURE 3A

```
     387            396            405            414            423            432
GCA TTT GAA ACA ACA ATG GGC TAT CAG TCA GGT GAA TTA ATA GGG AAG GAG TTA
 A   F   E   T   T   M   G   Y   Q   S   G   E   L   I   G   K   E   L 441            450            459            468            477            486
GGA GAA GTG CCT ATA AAT GAA AAA AAG GCT GAC TTG CTC GAT ACT ATA AAT TCA
 G   E   V   P   I   N   E   K   K   A   D   L   L   D   T   I   N   S 495            504            513            522            531            540
TGC ATC AGG ATA GGC AAG GAG TGG CAA GGA ATT TAC TAT GCC AAA AAG AAA AAC
 C   I   R   I   G   K   E   W   Q   G   I   Y   Y   A   K   K   K   N 549            558            567            576            585            594
GGA GAT AAT ATA CAA CAA AAT GTG AAG ATA ATA CCT GTC ATT GGA CAG GGA GGA
 G   D   N   I   Q   Q   N   V   K   I   I   P   V   I   G   Q   G   G 603            612            621            630            639            648
AAA ATT AGA CAC TAT GTG TCC ATT ATC AGA GTG TGC AAT GGC AAC AAT AAG GCT
 K   I   R   H   Y   V   S   I   I   R   V   C   N   G   N   N   K   A 657            666            675            684            693            702
GAG AAA ATA TCC GAA TGT GTT CAG TCT GAC ACT CGT ACA GAT AAT CAG ACA GGC
 E   K   I   S   E   C   V   Q   S   D   T   R   T   D   N   Q   T   G 711            720            729            738            747            756
AAA CAT AAA GAC AGG AAA GGC TCA CTA GAC GTC AAA GCT GTT GCC TCC CGT
 K   H   K   D   R   K   G   S   L   D   V   K   A   V   A   S   R
```

FIGURE 3B

```
        765         774         783         792         801         810
GCA ACT GAA GTT TCC AGC CAG AGA CAC TCT TCC ATG GCC CGG ATA CAT TCC
 A   T   E   V   S   S   Q   R   H   S   S   M   A   R   I   H   S 819         828         837         846         855         864
ATG ACA ATT GAG GCG CCC ATC ACC AAG GTA ATC AAT GTT ATC AAT GCT GCC CAG
 M   T   I   E   A   P   I   T   K   V   I   N   V   I   N   A   A   Q 873         882         891         900         909         918
GAA AGT AGT CCC ATG CCT GTG ACA GAA GCC CTA GAC CGT GTG CTG GAA ATT CTA
 E   S   S   P   M   P   V   T   E   A   L   D   R   V   L   E   I   L 927         936         945         954         963         972
AGA ACC ACT GAG TTA TAT TCA CCA CAG TTT GGT GCT AAA GAT GAT GAT CCC CAT
 R   T   T   E   L   Y   S   P   Q   F   G   A   K   D   D   D   P   H 981         990         999        1008        1017        1026
GCC AAT GAC CTT GTT CTT GGG GGC TTA ATG TCT GAT GGT TTG CGA AGA CTA TCA GGG
 A   N   D   L   V   L   G   G   L   M   S   D   G   L   R   R   L   S   G 1035        1044        1053        1062        1071        1080
AAT GAA TAT GTT CTT TCA ACA AAA AAC ACT CAA ATG GTT TCA AGC AAT ATA ATC
 N   E   Y   V   L   S   T   K   N   T   Q   M   V   S   S   N   I   I 1089        1098        1107        1116        1125        1134
ACT CCC ATC TCC CTT GAT GAT GTC CCA CCA CGG ATA GCT CGG GCC ATG GAA AAT
 T   P   I   S   L   D   D   V   P   P   R   I   A   R   A   M   E   N

FIGURE 3C
```

```
      1143              1152              1161              1170              1179              1188
GAG GAA TAC TGG GAC TTT GAT ATT TTT GAA CTG GAG GCT GCC ACC CAC AAT AGG
 E   E   Y   W   D   F   D   I   F   E   L   E   A   A   T   H   N   R 1197              1206              1215              1224              1233              1242
CCT TTG ATT TAT CTT GGT CTC AAA ATG TTT GCT CGC TTT GGA ATC TGT GAA TTC
 P   L   I   Y   L   G   L   K   M   F   A   R   F   G   I   C   E   F 1251              1260              1269              1278              1287              1296
TTA CAC TGC TCC GAG TCA AGA ACG CTA AGA TCA TGG TTA CAA ATT ATC GAA GCC AAT
 L   H   C   S   E   S   R   T   L   R   S   W   L   Q   I   I   E   A   N 1305              1314              1323              1332              1341              1350
TAT CAC TCC TCC AAT CCC TAC CAC AAT TCT ACA CAT TCT GCT GAT GTG CTT CAT
 Y   H   S   S   N   P   Y   H   N   S   T   H   S   A   D   V   L   H 1359              1368              1377              1386              1395              1404
TAT CAT GCC TAT TTT CTC TCC AAG GAG AGG ATA AAG GAA ACT TTA GAT CCA ATT
 Y   H   A   Y   F   L   S   K   E   R   I   K   E   T   L   D   P   I 1413              1422              1431              1440              1449              1458
GCC ACT GCC GTC GCT GCA CTC ATC GCA GCC ACC ATT CAT GAT GTG GAT CAC CCT GGG
 A   T   A   V   A   A   L   I   A   A   T   I   H   D   V   D   H   P   G 1467              1476              1485              1494              1503              1512
GAT GAG GTC GCT GCA CTC TGT AAT GCT GGA AGT GAG CTG GCC CTG TTG TAC AAT
 D   E   V   A   A   L   C   N   A   G   S   E   L   A   L   L   Y   N 1467              1476              1485              1494              1503              1512
AGA ACC AAC TCC TTC CTG TGT AAT GCT GGA AGT GAG CTG GCC CTG TTG TAC AAT
 R   T   N   S   F   L   C   N   A   G   S   E   L   A   L   L   Y   N
```

FIGURE 3D

```
      1521             1530             1539             1548             1557             1566
GAC ACT GCT GTG CTG GAG AGC CAC CAT GCG GCC TTG GCC TTC CAG CTG ACC ACT
 D   T   A   V   L   E   S   H   H   A   A   L   A   F   Q   L   T   T 1575             1584             1593             1602             1611             1620
GGA GAT AAA TGC AAT ATA TTT AAA AAC ATG GAG AGG AAT GAT TAT CGG ACA
 G   D   K   C   N   I   F   K   N   M   E   R   N   D   Y   R   T 1629             1638             1647             1656             1665             1674
CTG CGC CAG GGG ATT ATC GAC ATG GTC TTA GCC ACA GAA ATG ACA AAG CAC TTT
 L   R   Q   G   I   I   D   M   V   L   A   T   E   M   T   K   H   F 1683             1692             1701             1710             1719             1728
GAG CAT GTC AAC AAA TTT GTC AAC AGC ATC AAC AAA CCC TTG GCA ACA CTA GAA
 E   H   V   N   K   F   V   N   S   I   N   K   P   L   A   T   L   E 1737             1746             1755             1764             1773             1782
GAA AAT GGG GAA ACT GAT AAA AAC CAG GAA GTG ATA AAC ACT ATG CTT AGG ACT
 E   N   G   E   T   D   K   N   Q   E   V   I   N   T   M   L   R   T 1791             1800             1809             1818             1827             1836
CCA GAG AAC CGG ACC CTA ATC AAA CGA ATG CTG ATT AAA TGT GCT GAT GTG TCC
 P   E   N   R   T   L   I   K   R   M   L   I   K   C   A   D   V   S 1845             1854             1863             1872             1881             1890
AAT CCC TGC CGA CCC CTG CAG TAC TGC ATC GAG TGG GCT GCA CGC ATT TCG GAA
 N   P   C   R   P   L   Q   Y   C   I   E   W   A   A   R   I   S   E
```

FIGURE 3E

```
      1899          1908          1917          1926          1935          1944
GAA TAT TTT TCT CAG ACT GAT GAA GAG AAG CAG CAG GGC TTA CCT GTG GTG ATG
 E   Y   F   S   Q   T   D   E   E   K   Q   Q   G   L   P   V   V   M 1953          1962          1971          1980          1989          1998
CCA GTG TTT GAC AGA AAT ACC TGC AGC ATC CCC AAA TCC CAA ATC TCT TTC ATT
 P   V   F   D   R   N   T   C   S   I   P   K   S   Q   I   S   F   I 2007          2016          2025          2034          2043          2052
GAT TAC TTC ATC ACA GAC ATG TTT GAT GCT TGG GAT GCC TTT GTA GAC CTG CCT
 D   Y   F   I   T   D   M   F   D   A   W   D   A   F   V   D   L   P 2061          2070          2079          2088          2097          2106
GAT TTA ATG CAG CAT CTT GAC AAC AAC TTT AAA TAC TGG AAA GGA CTG GAC GAA
 D   L   M   Q   H   L   D   N   N   F   K   Y   W   K   G   L   D   E 2115          2124          2133          2142          2151          2160
ATG AAG CTG CGG AAC CTC CGA CCA CCT CCT GAA TAG TGG GAG ACA CCA CCC AGA
 M   K   L   R   N   L   R   P   P   P   E   *

2169          2178          2187          2196          2205          2214
GCC CTG AAG CTT TGT TCC TTC GGT CAT TTG GAA TTC CTG AGG GCA GCC AGA GCT 2223          2232          2241          2250          2259          2268
CCT TGG TCC TTT CAG TAC TAG GCA GAA CAG CCC CCG ATC TGC ATA GCC TGT GAA
```

FIGURE 3F

```
         2277              2286              2295              2304              2313              2322
         AGC CCA CGG GGA CAT CAG TAA CCT TCT GCA GCC ACC ATC CAA TGC CAT TAC TGT
         2331              2340              2349              2358              2367              2376
         CAA GTG AGA CTT GGC CAC TGT AGC CTG GGC CTG CAG GAG CTC TTC AGA AAG
         2385              2394              2403              2412              2421              2430
         GCA CAT GAG GAC CAC GGT TTG CCT CAG TTT CTG GTA AAA CAC AAG GTC TGG AGT
         2439              2448              2457              2466              2475              2484
         GCC CCT GCA AAG GGT ATT GAT GGA CTT CCT GCC AGT GAC AGA GCA TGT CTA TTG
         2493              2502              2511              2520              2529              2538
         CAA ACA ATT CTC TCA GTT ACG TTC AGC ACT TAA GAA CGG CTA ATG GCA ATA GGA
         2547              2556              2565              2574              2583              2592
         TCT TTA GCA ACT TTT TCA CAT CAT AGA AGG TGC AAT CGC TCA CTT GGG AAC ACT
         2601              2610              2619              2628              2637              2646
         ACT GAG AGT GAC TTC TCT TTT AAA ATT GAG TAG CAG ATG AAA AAT TAA AAT TTG
         2655              2664              2673              2682              2691              2700
         AAC TTG ATT ATT AAT ATC AAT TAA AAT GTT TTA TTT ATT TTA TTA AAA GCT CAA
         2709              2718              2727              2736              2745              2754
         TAT TTT CTA TGA ATT CAA AAA TAC TTC AGA GCC AAA GCC AAC TTC AAA TAC CGT
```

FIGURE 3G

```
            2763                2772           2781                2790           2799                2808
GAC CAA ATT TAC ATG ATT CAT ATT TAT GCA TTA CTT GGT ATA CAG ACT TAT
     2817                2826           2835                2844           2853                2862
TTT CAT AAT GCA AAT TAA TAA AAT GAC ACT TTT ACT GCA CTA TAG AAA TAT TCA
     2871                2880           2889                2898           2907                2916
TGT ATG TTA AAC TTT TCT GAT TGA GGC TAA CTG GAA AAA GCT GGG GTC GTA TTC
     2925                2934           2943                2952           2961                2970
TAA GTG CTA AAG AAG GCT GCT TCT ACT GTA TAG AAC CCA GGG CTC TGA AAC AGC
     2979                2988           2997                3006           3015                3024
TCT AGC CGC CTA ATG CAC TTC ACA GGT AAC TCC CCA AGG TAA AAC TAG ACT CTC
     3033                3042           3051                3060           3069                3078
TTG TTG GTT CGC AAA GAA AAG TTA GGA CTT AAC ACT TTT TTC TAA AAT TTT ATA
     3087                3096           3105                3114           3123                3132
ATT CAA TTT CCA AAA GTC TAC TCT ATT TTA TAC TGT TTC TAC AAA ATA TTC CTT
     3141                3150           3159                3168           3177                3186
ATA AAA ACA AAG AAC AAA AAT TGA ATA TTT AAT GAA TTG ACA TTT TAT AAC CAA
```

FIGURE 3H

```
              3195           3204           3213      3222           3231           3240
              CCT GTT TTT ATC TAC GGT GGG AAT CTT TGA TGC CAG AAA TTT ATA AAG AGG TTC 3249           3258           3267      3276           3285           3294
              TGT ATC TTC ACA CCT TGA ATA AGC ATA ATA CCA TAA AAA ATG ACA CTT GAC ATG 3303           3312           3321      3330           3339           3348
              TCA ATG TAT TTG TCA TTT CAT TTT AAA CTC GTA TTT GTT TTT GTG TTC CCA GAT 3357           3366           3375      3384           3393
              AAA AAT GAA ATT AAA CCA TTT CTT TTT AAG AAA AAA AAA AAA AAA AAA  3'
```

FIGURE 3I

```
                9           18          27          36          45          54
5' GCC CTT GAA TGC TTT GAT AAG CAT CAT GAA ATT ATT GTA ATT GAT CAT AGA
   A   L   E   C   F   D   K   H   H   E   I   I   V   I   D   H   R 63          72          81          90          99         108
   CAA ACT CAG AAC TTC GAT GCA GAA CTC GCA GTG TGC AGG TCG ATC CGG GCC ACA AAT
   Q   T   Q   N   F   D   A   E   L   A   V   C   R   S   I   R   A   T   N 117         126         135         144         153         162
   CCC TCC GAG CAC ACG GTG ATC CTC GCA GTG GTT TCG CGA GTA TCG GAT GAC CAT
   P   S   E   H   T   V   I   L   A   V   V   S   R   V   S   D   D   H 171         180         189         198         207         216
   GAA GAG GCG TCA GTC CTT CCT CTT CTC CAC GCA GGC TTC AAC AGG AGA TTT ATG
   E   E   A   S   V   L   P   L   L   H   A   G   F   N   R   R   F   M 225         234         243         252         261         270
   GAG AAT AGC AGC ATA ATT GCT TGC TAT AAT GAA CTG ATT CAA ATA GAA CAT GGG
   E   N   S   S   I   I   A   C   Y   N   E   L   I   Q   I   E   H   G 279         288         297         306         315         324
   GAA GTT CGC TCC CAG TTC AAA TTA CGG GCC TGT AAT TCA GTG TTT ACA GCA TTA
   E   V   R   S   Q   F   K   L   R   A   C   N   S   V   F   T   A   L 333         342         351         360         369         378
   GAT CAC TGT CAT GAA GCC ATA GAA ATA ACA AGC GAT GAC CAC GTG ATT CAG TAT
   D   H   C   H   E   A   I   E   I   T   S   D   D   H   V   I   Q   Y
```

FIGURE 4A

| | 387 | | | 396 | | | 405 | | | 414 | | | 423 | | | 432 |
|---|---|---|---|---|---|---|---|---|---|---|---|---|---|---|---|---|
| GTC | AAC | CCA | GCC | TTC | GAA | AGG | ATG | GGC | TAC | CAC | AAA | GGT | GAG | CTC | CTG | GGA |
| V | N | P | A | F | E | R | M | G | Y | H | K | G | E | L | L | G |

| | | | | 441 | | | 450 | | | 459 | | | 468 | | | 477 | | | 486 |
|---|---|---|---|---|---|---|---|---|---|---|---|---|---|---|---|---|---|---|---|
| AAA | GAA | CTC | GCT | GAT | CTG | CCC | AAA | AGC | GAT | AAG | AAC | CGG | GCA | GAC | CTT | CTC | GAC |
| K | E | L | A | D | L | P | K | S | D | K | N | R | A | D | L | L | D |

| | 495 | | | 504 | | | 513 | | | 522 | | | 531 | | | 540 |
|---|---|---|---|---|---|---|---|---|---|---|---|---|---|---|---|---|
| ACC | ATC | AAT | ACA | TGC | AAG | AAG | GGA | AAG | GAG | TGG | CAG | GGG | GTT | TAC | TAT | GCC |
| T | I | N | T | C | K | K | G | K | E | W | Q | G | V | Y | Y | A |

| | 549 | | | 558 | | | 567 | | | 576 | | | 585 | | | 594 |
|---|---|---|---|---|---|---|---|---|---|---|---|---|---|---|---|---|
| AGA | CGG | AAA | TCC | GGG | GAC | AGC | ATC | CAA | CAG | CAC | GTG | AAG | ATC | ACC | CCA | GTG | ATT |
| R | R | K | S | G | D | S | I | Q | Q | H | V | K | I | T | P | V | I |

| | 603 | | | 612 | | | 621 | | | 630 | | | 639 | | | 648 |
|---|---|---|---|---|---|---|---|---|---|---|---|---|---|---|---|---|
| GGC | CAA | GGG | AAA | ATT | AGG | CAT | TTT | GTC | TCG | CTC | AAG | AAA | CTG | TGT | TGT | ACC |
| G | Q | G | K | I | R | H | F | V | S | L | K | K | L | C | C | T |

| | 657 | | | 666 | | | 675 | | | 684 | | | 693 | | | 702 |
|---|---|---|---|---|---|---|---|---|---|---|---|---|---|---|---|---|
| ACT | GAC | AAT | AAT | AAG | CAG | ATT | CAC | AAG | ATT | CAT | CGT | GAT | TCA | GGA | GAC | AAT | TCT |
| T | D | N | N | K | Q | I | H | K | I | H | R | D | S | G | D | N | S |

| | 711 | | | 720 | | | 729 | | | 738 | | | 747 | | | 756 |
|---|---|---|---|---|---|---|---|---|---|---|---|---|---|---|---|---|
| CAG | ACA | GAG | CCT | CAT | TCA | TTC | AGA | TAT | AAG | AAC | AGG | AGG | AAA | GAG | TCC | ATT | GAC |
| Q | T | E | P | H | S | F | R | Y | K | N | R | R | K | E | S | I | D |

FIGURE 4B

```
765              774              783              792              801              810
GTG AAA TCG ATA TCA TCT CGA GGC AGT GAT GCA CCA AGC CTG CAG AAT CGT CGC
 V   K   S   I   S   S   R   G   S   D   A   P   S   L   Q   N   R   R 819              828              837              846              855              864
TAT CCG TCC ATG GCG AGG ATC CAC TCC ATG ACC ATC GAG GCT CCC ACA AAG
 Y   P   S   M   A   R   I   H   S   M   T   I   E   A   P   I   T   K 873              882              891              900              909              918
GTT ATA AAT ATA ATC AAT GCA GCC CAA GAA AAC AGC CCA GTC ACA GTA GCG GAA
 V   I   N   I   I   N   A   A   Q   E   N   S   P   V   T   V   A   E 927              936              945              954              963              972
GCC TTG GAC AGA GTT CTA GAG ATT TTA CGG ACC ACA GAA CTG TAC TCC CCT CAG
 A   L   D   R   V   L   E   I   L   R   T   T   E   L   Y   S   P   Q 981              990              999              1008             1017             1026
CTG GGT ACC AAA GAT GAA GAT CCC CAC ACC AGT GAT CTT GTT GGA GGC CTG ATG
 L   G   T   K   D   E   D   P   H   T   S   D   L   V   G   G   L   M 1035             1044             1053             1062             1071             1080
ACT GAC GGC TTG AGA AGA CTG TCA GGA AAC GAG TAT GTG TTT ACT AAG AAT GTG
 T   D   G   L   R   R   L   S   G   N   E   Y   V   F   T   K   N   V 1089             1098             1107             1116             1125             1134
CAC CAG AGT CAC AGT CAC CTT GCA ATG CCA ATA ACC ATC AAT GAT GTT CCC CCT
 H   Q   S   H   S   H   L   A   M   P   I   T   I   N   D   V   P   P
```

FIGURE 4C

```
       1143              1152              1161              1170              1179              1188
TGT ATC TCT CAA TTA CTT GAT AAT GAG GAG AGT TGG GAC TTC AAC ATC TTT GAA
 C   I   S   Q   L   L   D   N   E   E   S   W   D   F   N   I   F   E 1197              1206              1215              1224              1233              1242
TTG GAA GCC ATT ACG CAT AAA AGG CAT CCA TTG GTT TAT CTG GGC TTA AAG GTC TTC
 L   E   A   I   T   H   K   R   H   P   L   V   Y   L   G   L   K   V   F 1251              1260              1269              1278              1287              1296
TCT CGG TTT GGA GTA TGT GAG TTT TTA AAC TGT TCT GAA ACC ACT CTT CGG GCC
 S   R   F   G   V   C   E   F   L   N   C   S   E   T   T   L   R   A 1305              1314              1323              1332              1341              1350
TGG TTC CAA GTG ATC GAA GCC AAC TAC CAC TCT TCC AAT GCC TAC CAC AAC TCC
 W   F   Q   V   I   E   A   N   Y   H   S   S   N   A   Y   H   N   S 1359              1368              1377              1386              1395              1404
ACC CAT GCT GCC GAC GTC CTG CAC GCC ACC GCT TTC TTT CTT GGA AAG GAA AGA
 T   H   A   A   D   V   L   H   A   T   A   F   F   L   G   K   E   R 1413              1422              1431              1440              1449              1458
GTA AAG GGA AGC CTC GAT CAG TTG GAT GAG GTG GCA GCC CTC ATT GCT GCC ACA
 V   K   G   S   L   D   Q   L   D   E   V   A   A   L   I   A   A   T 1467              1476              1485              1494              1503              1512
GTC CAT GAC GTG GAT CAC CCG GGA AGG ACC AAC TCT TTC CTC TGC AAT GCA GGC
 V   H   D   V   D   H   P   G   R   T   N   S   F   L   C   N   A   G

FIGURE 4D
```

```
    1521        1530             1539             1548             1557             1566
AGT GAG CTT GCT GTG CTT TAC AAT GAC ACT GCT GTT CTG GAG AGT CAC CAC ACC
 S   E   L   A   V   L   Y   N   D   T   A   V   L   E   S   H   H   T 1575             1584             1593             1602             1611             1620
GCC CTG GCC TTC CAG CTC ACG GTC AAG GAC ACC AAA TGC AAC ATT TTC AAG AAT
 A   L   A   F   Q   L   T   V   K   D   T   K   C   N   I   F   K   N 1629             1638             1647             1656             1665             1674
ATT GAC AGG AAC CAT TAT CGA ACG CTG CGC CAG GCT ATT ATT GAC ATG GTT TTG
 I   D   R   N   H   Y   R   T   L   R   Q   A   I   I   D   M   V   L 1683             1692             1701             1710             1719             1728
GCA ACA GAG ATG ACA AAA CAC TTT GAA CAT GTG AAT AAG TTT GTG AAC AGC ATC
 A   T   E   M   T   K   H   F   E   H   V   N   K   F   V   N   S   I 1737             1746             1755             1764             1773             1782
AAC AAG CCA ATG GCA GCT GAG ATT GAA GGC AGC GAC TGT GAA TGC AAC CCT GCT
 N   K   P   M   A   A   E   I   E   G   S   D   C   E   C   N   P   A 1791             1800             1809             1818             1827             1836
GGG AAG AAC TTC CCT GAA AAC CAA ATC CTG ATC AAA CGC ATG ATG ATT AAG TGT
 G   K   N   F   P   E   N   Q   I   L   I   K   R   M   M   I   K   C 1845             1854             1863             1872             1881             1890
GCT GAC GTG GCC AAC CCA TGC CGC CCC TTG GAC CTG TGC ATT GAA TGG GCT GGG
 A   D   V   A   N   P   C   R   P   L   D   L   C   I   E   W   A   G
```

FIGURE 4E

```
      1899      1908      1917      1926      1935      1944
AGG ATC TCT GAG GAG TAT TTT GCA CAG ACT GAT GAG AAG AGA CAG GGA CTA
 R   I   S   E   E   Y   F   A   Q   T   D   E   E   K   R   Q   G   L
      1953      1962      1971      1980      1989      1998
CCT GTG GTG ATG CCA GTG TTT GAC CGG AAT ACC TGT AGC ATC CCC AAG TCT CAG
 P   V   V   M   P   V   F   D   R   N   T   C   S   I   P   K   S   Q
      2007      2016      2025      2034      2043      2052
ATC TCT TTC ATT GAC TAC TTC ATA ACA GAC ATG TTT GAT GCT TGG GAT GCC TTT
 I   S   F   I   D   Y   F   I   T   D   M   F   D   A   W   D   A   F
      2061      2070      2079      2088      2097      2106
GCA CAT CTG CCA GCC CTG ATG CAA CAT TTG GCT GAC AAC TAC AAA CAC TGG AAG
 A   H   L   P   A   L   M   Q   H   L   A   D   N   Y   K   H   W   K
      2115      2124      2133      2142      2151      2160
ACA CTA GAT GAC CTA AAG TGC AAA AGT TTG AGG CTT CCA TCT GAC AGC TAA AGC
 T   L   D   D   L   K   C   K   S   L   R   L   P   S   D   S   *
      2169      2178      2187      2196      2205      2214
CAA GCC ACA GAG GGG GCC TCT TGA CCG ACA AAG GAC ACT GTG AAT CAC AGT AGC
      2223      2232      2241      2250      2259      2268
GTA AAC GAG AGG CCT TCC TTT CTA ATG ACA ATG GGT ATT GGT GAA GGA GCT
```

FIGURE 4F

```
     2277       2286       2295       2304       2313       2322
AAT GTT TAA TAT TTG ACC TTG AAT CAT TCA AGT CCC CAA ATT TCA TTC TTA GAA
     2331       2340       2349       2358       2367       2376
AGT TAT GTT CCA TGA AGA AAA ATA TAT GTT CTT TTG AAT ACT TAA TGA CAG AAC
     2385       2394       2403       2412       2421       2430
AAA TAC TTG GCA AAC TCC TTT GCT CTG CTG TCA TCC TGT GTA CCC TTG TCA ATC
     2439       2448       2457       2466       2475       2484
CAT GGA GCT GGT TCA CTG TAA CTA GCA GGC CAC AGG AAG CAA AGC CTT GGT GCC
     2493       2502       2511       2520       2529       2538
TGT GAG CTC ATC TCC CAG GAT GGT GAC TAA GTA GCT TAG CTA GTG ATC AGC TCA
     2547       2556       2565       2574       2583       2592
TCC TTT ACC ATA AAA GTC ATC ATT GCT GTT TAG CTT GAC TGT TTT CCT CAA GAA
     2601       2610       2619       2628       2637       2646
CAT CGA TCT GAA GGA TTC ATA AGG AGC TTA TCT GAA CAG ATT TAT CTA AAA AAA
     2655
AAA AAA AAA AA 3'
```

FIGURE 4G

```
  1 -LACFLDKHHDIIIIDHRNPRQLDAEALCRSIRSSKLSEN  PDE8A(E)
  1 ALECFLDKHHEIIVIDHRQTQNFDAEAVCRSIRATNPSEH  PDE8B(E)
  1 ---------------------------------------  PDE8A
  1 ---------------------------------------  PDE8B
  1 ---------------------------------------  g1705952

40 TVIVGVVRRV--DREELSVMPFISAGFTRRYVENPNIMAC  PDE8A(E)
 41 TVILAVVSRVSDDHEEASVLPLHAGFNRRFMENSSIIAC   PDE8B(E)
  1 ------------MPLVD--F----FCE------TC      PDE8A
  1 ---------------------------------------  PDE8B
  1 ---------------------------------------  g1705952

78 YNELLQLEFGEVRSQLKLRACNSVFTALENSEDAIEITSE  PDE8A(E)
 81 YNELIQIEHGEVRSQFKLRACNSVFTALDHCHEAIEITSD  PDE8B(E)
  1 ---------------------------------------  PDE8A
  1 ---------------------------------------  PDE8B
 12 SKPWL----VGWWDQFK----------------------  g1705952

118 DRFIQYANPAFETTMGYQSGELIGKELGEVPINEK-KADL  PDE8A(E)
121 DHVIQYVNPAFERMMGYHKGELLGKELADLPKSDKNRADL  PDE8B(E)
  1 ---------------------------------------  PDE8A
  1 ---------------------------------------  PDE8B
 25 ---RMLNRELTHL--SEMSRS--                  g1705952
```

FIGURE 5A

```
157 L D T I N S C I R I G K E W Q G I Y Y A K K K N G D N I Q Q N V K I I P V I G Q        PDE8A(E)
161 L D T I N T C I K K G K E W Q G V V Y Y A R R K S G D S I Q Q H V K I T P V I G Q        PDE8B(E)
  1 - - - - - - - - - - - - - - - - - - - - - - - - - - - - - - - - - - - - - - - -        PDE8A
  1 - - - - - - - - - - - - - - - - - - - - - - - - - - - - - - - - - - - - - - - -        PDE8B
 41 - - - - - - - - - - - - - - - - - - - - - - - - - - - - - - - - - - - - - - - -        g1705952

197 G G K I R H Y V S L I I R V C - - N G N N K A E K I S E C V Q S D T R T D N Q T          PDE8A(E)
201 G G K I R H F V S L K K L C T T D N N K Q I H K I H R D S G D N S Q T E P H S            PDE8B(E)
  1 - - - - - - - - - - - - - - - - - - - - - - - - - - - - - - - - - - - - - -            PDE8A
  1 - - - - - - - - - - - - - - - - - - - - - - - - - - - - - - - - - - - - - -            PDE8B
 41 G N Q V S E Y I S N T F L - - - - - - - - - - - - - - - - - - - - - - - - - -            g1705952

234 G K H K D R R K G S L D V K A V A S R A T E V S S - - Q R R H S S M A R I H S M          PDE8A(E)
241 F R Y K N R R K E S I D V K S I S S R G S D A P S L Q N R R Y P S M A R I H S M          PDE8B(E)
  1 - - - - - - - - - - - - - - - - - - - - - - - - - - - - - - - M A R I H S M            PDE8A
  1 - - - - - - - - - - - - - - D K Q N E V E I P S P T P R Q R - - A F Q Q P P P S V L R Q S Q P M  PDE8B
 54 - - - - - - - - - - - - - - - - - - - - - - - - - - - - - - - - - - - - - - -            g1705952

272 T I E A P I T K V I N V I N A A Q E S S P M P V T E A L D R V L E I L R T T E L          PDE8A(E)
281 T I E A P I T K V I N I I N A A Q E N S P V T V A E A L D R V L E I L R T T E L          PDE8B(E)
  8 T I E A P I T K V I N I I N A A Q E S S P M P V T E A L D R V L E I L R T T E L          PDE8A
  1 - - - - - - - - - - - - - - - - - - - - - - - - - - - - - - - - - - - - - - -            PDE8B
 86 S Q I T G L K K L V H - - - - - - - - - - - - - - - - - - T G S L N T N V - - -            g1705952
```

```
312 Y S P Q F G A K D D D P H A N D L V G G L M S D G L R R L S G N E Y V L S T K N    PDE8A(E)
321 Y S P Q L G T K D E D P H T S D L V G G L M T D G L R R L S G N E Y V F - T K N    PDE8B(E)
 48 Y S P Q F G A K D D D P H A N D L V G G L M S D G L R R L S G N E Y V L S T K N    PDE8A
  1 - - - - - - - - - - - - - - - - - - - - - - - - - - - - - - - - - - - - - -    PDE8B
105 - - P R F G V K T D Q - - - - - - - - - - - - - - - - E D L L A Q E L E N L S K    g1705952

352 T Q M V S S N I I T P I S L D D V P P R I A R A M E N E E Y W D F D I F E L E A    PDE8A(E)
360 V H Q S H S H L A M P I T I N D V P P C I S Q L L D N E E S W D F N I F E L E A    PDE8B(E)
 88 T Q M V S S N I I T P I S L D D V P P R I A R A M E N E E Y W D F D I F E L E V    PDE8A
  1 - - - - - - - - - - - - - - - - - - - - - - - - - - - - - - - - - - - - - -    PDE8B
127 - - - - - - - - - - - - - - - - - - - - - - - - - - - W G L N I F C V S E E    g1705952

392 A T H N R P L I Y L G L K M F A R F G I C E F L H C S E S T L R S W L Q I I E A    PDE8A(E)
400 I T H K R P L V Y L G L K V F S R F G V C E F L N C S E T T L R A W F Q V I E A    PDE8B(E)
128 A T H N R P L I Y L G L K M F A R F G I C E F L H C S E S T L R S W L Q I I E A    PDE8A
  1 - - - - - - - - - - - - - - - - - - - - - - - - - - - - - - - - - - - - - -    PDE8B
137 Y A G G R S L S C I M Y T I F Q E R D L L K K F H I P V D T M M M Y M L T L E D    g1705952

432 N Y H S S N P Y H N S T H S A D V L H A T A Y F L S K E R I K E T L D P I D E V    PDE8A(E)
440 N Y H S S N A Y H N S T H A A D V L H A T A F F L G K E R V K G S L D Q L D E V    PDE8B(E)
168 N Y H S S N P Y H N S T H S A D V L H A T A Y F L S K E R I K E T L D P I D E V    PDE8A
  1 - - - - - - - - - - - - - - - - - - - - - - - - - - - - - - - - - - - - - -    PDE8B
177 H Y H A D V A Y H N S L H A A D V L Q S T H V L L A T P A L D A V F T D L E I L    g1705952
```

FIGURE 5D

```
472  A A L I A A T I H D V D H P G R T N S F L C N A G S E L A I L Y N D T A V L E S    PDE8A(E)
480  A A L I A A T V H D V D H P G R T N S F L C N A G S E L A V L Y N D T A V L E S    PDE8B(E)
208  A A L I A A T I H D V D H P G R T N S F L C N A G S E L A I L Y N D T A V L E S    PDE8A
1    - - - - - - - - - - - - - - - - - - - - - - - - - - - - - - - - - - - - -        PDE8B
217  A A L F A A A I H D V D H P G V S N Q F L I N T N S E L A L M Y N D E S V L E N    g1705952

512  H H A A L A F Q L T T G D D K C N I F K N M E R N D Y R T L R Q G I I D M V L A    PDE8A(E)
520  H H T A L A F Q L T K C N I F K N I D R N H Y R T L R Q A I I D M V L A            PDE8B(E)
248  H H A A L A F Q L T T G D D K C N I F K N M E R N D Y R T L R Q G I I D M V L A    PDE8A
1    - - - - - - - - - - - - - - - - - - - - - - - - - - - - - - - - - - - -          PDE8B
257  H H L A V G F K L - L Q E E N C D I F Q N L S K R Q R Q S L R K M V I D M V L A    g1705952

552  T E M T K H F E H V N K F V N S I N K P L A T L E E N G E T D K N Q E V I N T M    PDE8A(E)
560  T E M T K H F E H V N K F V N S I N K P M A A E I E G S D C E C N P A G K N F -    PDE8B(E)
288  T E M T R H F E H V N K F V N S I N K P L A T L E E N G E T D K N Q E V I N T M    PDE8A
1    - - - - - - - - - - - - I N K P M A A E I E G S D C E C N P A G K N F -          PDE8B
296  - - - T D M S K H M T L - - - - - - - - - L A D L K T M V E T K K V T S S G V L L  g1705952

592  L R T P E N R T L I K R M L I K C A D V S N P C R P L Q Y C I E W A A R I S E E    PDE8A(E)
599  - - P E N Q I L I K R M M I K C A D V A N P C R P L D L C I E W A G R I S E E     PDE8B(E)
328  L R T P E N R T L I K R M L I K C A D V S N P C R P L Q Y C I E W A A R I S E E    PDE8A
24   - - P X N Q I L I K X M M I K C A X X N P C R P L D L C I E W A G R I S E E       PDE8B
325  L D N Y S D R I Q V L R N M V H C A D L S N P T K P L E L Y R Q W T D R I M A E    g1705952
```

```
632 Y F S Q T D E E K Q Q G L P V V M P V F D R N T C S I P K S Q I S F I D Y F I T   PDE8A(E)
636 Y F A Q T D E E K R Q G L P V V M P V F D R N T C S I P K S Q I S F I D Y F I T   PDE8B(E)
368 Y F S Q T D E E K Q Q G L P V V M P V F D R N T C S I P K S Q I S F I D Y F I T   PDE8A
 61 Y F A Q T D E E K R Q G L P V V M X V F D                                          PDE8B
365 F F Q Q G D R E R E R G M E I S - P M C D K H T A S V E K S Q V G F I D Y I V H   g1705952

672 D M F D A W D A F V D L P D L M Q H L D N N F K Y W K G L D E M K L R N L R P P   PDE8A(E)
676 D M F D A W D A F A H L P A L M Q H L A D N Y K H W K T L D D L K C K S L R L P   PDE8B(E)
408 D M F D A W D A F V D L P D L M Q H L D N N F K Y W K G L D E M K L R N L R P P   PDE8A
 81                                                                                   PDE8B
404 P L W E T W A D L V H P D A Q D I L D T L E D N R D W Y H S A I R Q S P S P P L   g1705952

712 P E                                                                               PDE8A(E)
716 S D S                                                                             PDE8B(E)
448 P E                                                                               PDE8A
 81                                                                                   PDE8B
444 E E E P G G L G H P S L P D K F Q F E L T L E E E E E D S L E V P G L P T T E     g1705952

713                                                                                   PDE8A(E)
718                                                                                   PDE8B(E)
449                                                                                   PDE8A
 81                                                                                   PDE8B
484 E T F L A A E D A R A Q A V D W S K V K G P S T T V V E V A E R L K Q E T A S A   g1705952
```

FIGURE 5E

| | | |
|---|---|---|
| 713 | Y G A P Q E S M E A V G C S F S P G T P I L P D V R T L S S S E E A P G L L G L | PDE8A(E) |
| 718 | | PDE8B(E) |
| 449 | | PDE8A |
| 81 | | PDE8B |
| 524 | | g1705952 |
| 713 | P S T A A E V E A P R D H L A A T R A C S A C S G T S G D N S A I I S A P G R W | PDE8A(E) |
| 718 | | PDE8B(E) |
| 449 | | PDE8A |
| 81 | | PDE8B |
| 564 | | g1705952 |
| 713 | | PDE8A(E) |
| 718 | | PDE8B(E) |
| 449 | | PDE8A |
| 81 | | PDE8B |
| 604 | G S G G D P A | g1705952 |

FIGURE 5F

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
       (A) LENGTH: 449 amino acids
       (B) TYPE: amino acid
       (C) STRANDEDNESS: single
       (D) TOPOLOGY: linear (vii) IMMEDIATE SOURCE:
       (A) LIBRARY: THPIPLB02
       (B) CLONE: 156196

(xi) SEQUENCE DESCRIPTION: SEQ ID NO:1:

Met Ala Arg Ile His Ser Met Thr Ile Glu Ala Pro Ile Thr Lys Val
 1               5                  10                  15

Ile Asn Ile Ile Asn Ala Ala Gln Glu Ser Ser Pro Met Pro Val Thr
                20                  25                  30

Glu Ala Leu Asp Arg Val Leu Glu Ile Leu Arg Thr Thr Glu Leu Tyr
            35                  40                  45

Ser Pro Gln Phe Gly Ala Lys Asp Asp Pro His Ala Asn Asp Leu
        50                  55                  60

Val Gly Gly Leu Met Ser Asp Gly Leu Arg Arg Leu Ser Gly Asn Glu

```
               65                  70                  75                  80
Tyr Val Leu Ser Thr Lys Asn Thr Gln Met Val Ser Ser Asn Ile Ile
                         85                  90                  95

Thr Pro Ile Ser Leu Asp Asp Val Pro Pro Arg Ile Ala Arg Ala Met
                100                 105                 110

Glu Asn Glu Glu Tyr Trp Asp Phe Asp Ile Phe Glu Leu Glu Val Ala
            115                 120                 125

Thr His Asn Arg Pro Leu Ile Tyr Leu Gly Leu Lys Met Phe Ala Arg
        130                 135                 140

Phe Gly Ile Cys Glu Phe Leu His Cys Ser Glu Ser Thr Leu Arg Ser
145                 150                 155                 160

Trp Leu Gln Ile Ile Glu Ala Asn Tyr His Ser Ser Asn Pro Tyr His
                165                 170                 175

Asn Ser Thr His Ser Ala Asp Val Leu His Ala Thr Ala Tyr Phe Leu
                180                 185                 190

Ser Lys Glu Arg Ile Lys Glu Thr Leu Asp Pro Ile Asp Glu Val Ala
            195                 200                 205

Ala Leu Ile Ala Ala Thr Ile His Asp Val Asp His Pro Gly Arg Thr
        210                 215                 220

Asn Ser Phe Leu Cys Asn Ala Gly Ser Glu Leu Ala Ile Leu Tyr Asn
225                 230                 235                 240

Asp Thr Ala Val Leu Glu Ser His His Ala Ala Leu Ala Phe Gln Leu
                245                 250                 255

Thr Thr Gly Asp Asp Lys Cys Asn Ile Phe Lys Asn Met Glu Arg Asn
                260                 265                 270

Asp Tyr Arg Thr Leu Arg Gln Gly Ile Ile Asp Met Val Leu Ala Thr
            275                 280                 285

Glu Met Thr Arg His Phe Glu His Val Asn Lys Phe Val Asn Ser Ile
        290                 295                 300

Asn Lys Pro Leu Ala Thr Leu Glu Glu Asn Gly Glu Thr Asp Lys Asn
305                 310                 315                 320

Gln Glu Val Ile Asn Thr Met Leu Arg Thr Pro Glu Asn Arg Thr Leu
                325                 330                 335

Ile Lys Arg Met Leu Ile Lys Cys Ala Asp Val Ser Asn Pro Cys Arg
                340                 345                 350

Pro Leu Gln Tyr Cys Ile Glu Trp Ala Ala Arg Ile Ser Glu Glu Tyr
            355                 360                 365

Phe Ser Gln Thr Asp Glu Glu Lys Gln Gln Gly Leu Pro Val Val Met
        370                 375                 380

Pro Val Phe Asp Arg Asn Thr Cys Ser Ile Pro Lys Ser Gln Ile Ser
385                 390                 395                 400

Phe Ile Asp Tyr Phe Ile Thr Asp Met Phe Asp Ala Trp Asp Ala Phe
                405                 410                 415

Val Asp Leu Pro Asp Leu Met Gln His Leu Asp Asn Asn Phe Lys Tyr
            420                 425                 430

Trp Lys Gly Leu Asp Glu Met Lys Leu Arg Asn Leu Arg Pro Pro Pro
        435                 440                 445

Glu (2) INFORMATION FOR SEQ ID NO:2:

(i) SEQUENCE CHARACTERISTICS:
        (A) LENGTH: 2201 base pairs
        (B) TYPE: nucleic acid
```

```
        (C) STRANDEDNESS: single
        (D) TOPOLOGY: linear (vii) IMMEDIATE SOURCE:
         (A) LIBRARY: THPIPLB02
         (B) CLONE: 156196

(xi) SEQUENCE DESCRIPTION: SEQ ID NO:2:

CGATACTATA AATTCATGCA TCAGGATAGG CAAGGAGTGG CAAGGAATTT ACTATGCCAA      60

AAAGAAAAAC GGAGATAATA TACAACAAAA TGTGAAGATA ATACCTGTCA TTGGACAGGG     120

AGGAAAAATT AGACACTATG TGTCCATTAT CAGAGTGTGC AATGGCAACA ATAAGGCTGA     180

GAAAATATCC GAATGTGTTC AGTCTGACAC TCATACAGAT AATCAGACAG GCAAACATAA     240

AGACAGGAGA AAAGGCTCAC TAGACGTCAA AGCTGTTGCC TCCCGTGCAA CTGAAGTTTC     300

CAGCCAGAGA CGACACTCTT CCATGGCCCG GATACATTCC ATGACAATTG AGGCGCCCAT     360

CACCAAGGTA ATCAATATTA TCAATGCTGC CCAGGAAAGT AGTCCCATGC CTGTGACAGA     420

AGCCCTAGAC CGTGTGCTGG AAATTCTAAG AACCACTGAG TTATATTCAC CACAGTTTGG     480

TGCTAAAGAT GATGATCCCC ATGCCAATGA CCTTGTTGGG GGCTTAATGT CTGATGGTTT     540

GCGAAGACTA TCAGGGAATG AATATGTTCT TTCAACAAAA AACACTCAAA TGGTTTCAAG     600

CAATATAATC ACTCCCATCT CCCTTGATGA TGTCCCACCA CGGATAGCTC GGGCCATGGA     660

AAATGAGGAA TACTGGGACT TTGATATTTT TGAACTGGAG GTTGCCACCC ACAATAGGCC     720

TTTGATTTAT CTTGGTCTCA AAATGTTTGC TCGCTTTGGA ATCTGTGAAT TCTTACACTG     780

CTCCGAGTCA ACGCTAAGAT CATGGTTACA AATTATCGAA GCCAATTATC ATTCCTCCAA     840

TCCCTACCAC AATTCTACAC ATTCTGCTGA TGTGCTTCAT GCCACTGCCT ATTTTCTCTC     900

CAAGGAGAGG ATAAAGGAAA CTTTAGATCC AATTGATGAG GTCGCTGCAC TCATCGCAGC     960

CACCATTCAT GATGTGGATC ACCCTGGGAG AACCAACTCC TTCCTGTGTA ATGCTGGAAG    1020

TGAGCTGGCC ATTTTGTACA ATGACACTGC TGTGCTGGAG AGCCACCATG CGGCCTTGGC    1080

CTTCCAGCTG ACCACTGGAG ATGATAAATG CAATATATTT AAAAACATGG AGAGGAATGA    1140

TTATCGGACA CTGCGCCAGG GGATTATCGA CATGGTCTTA GCCACAGAAA TGACAAGGCA    1200

CTTTGAGCAT GTCAACAAAT TTGTCAACAG CATCAACAAA CCCTTGGCAA CACTAGAAGA    1260

AAATGGGGAA ACTGATAAAA ACCAGGAAGT GATAAACACT ATGCTTAGGA CTCCAGAGAA    1320

CCGGACCCTA ATCAAACGAA TGCTGATTAA ATGTGCTGAT GTGTCCAATC CCTGCCGACC    1380

CCTGCAGTAC TGCATCGAGT GGGCTGCACG CATTTCGGAA GAATATTTTT CTCAGACTGA    1440

TGAAGAGAAG CAGCAGGGCT TACCTGTGGT GATGCCAGTG TTTGACAGAA ATACCTGCAG    1500

CATCCCCAAA TCCCAAATCT CTTTCATTGA TTACTTCATC ACAGACATGT TGATGCTTG    1560

GGATGCCTTT GTAGACCTGC TGATTTAAT GCAGCATCTT GACAACAACT TTAAATACTG     1620

GAAAGGACTG GACGAAATGA AGCTGCGGAA CCTCCGACCA CCTCCTGAAT AGTGGGAGAC    1680

ACCACCCAGA GCCCTGAAGC TTTGTTCCTT CGGTCATTTG GAATTCCTGA GGGCARACCA    1740

GAGCTCCTTG GTCCTTTCAG TRCWAGGCAG NANACAGCCC CCGATCTGYA TAGCCTGTGA    1800

AAGCCCRCGG GGACATCAGT AACCTTCTKC AGCCACCATC CAATGCCATT ACTGTCAAGT    1860

GAGACTTGGC CMCTGTARCC TGGGCCTKCT KCAGGAGCTC TTCAGAAAGG CACATKAGGA    1920

CCACGGNTTT SGCTCAGTTT CTGGTAAAAC ACAAGGTCTG GAGTKCCCCT GCMAAGGGTA    1980

TTGATGGACT TCCTKCCAGT GACAGAGCAT GTCTATTTCC AACAATTCTC TCANTTACGT    2040

TCAACACTTA AGAACGGCTA ATGGCAATAG GATCTTTAAC AACTTTTTCA CATCANAGNA    2100
```

```
GGTTCAATCG CTCACTTGGG NACACNACTG AGAGTGACTT CTCTTTTAAA ATTGAGTAAC      2160

AGATGGAAAA ATAAAATTTG GACTTGATTA TTAANATCCC N                          2201
```

(2) INFORMATION FOR SEQ ID NO:3:

(i) SEQUENCE CHARACTERISTICS:
        (A) LENGTH: 81 amino acids
        (B) TYPE: amino acid
        (C) STRANDEDNESS: single
        (D) TOPOLOGY: linear (vii) IMMEDIATE SOURCE:
        (A) LIBRARY: LATRNOT01
        (B) CLONE: 464655

(xi) SEQUENCE DESCRIPTION: SEQ ID NO:3:

```
Ile Asn Lys Pro Met Ala Ala Glu Ile Glu Gly Ser Asp Cys Glu Cys
1               5                   10                  15

Asn Pro Ala Gly Lys Asn Phe Pro Xaa Asn Gln Ile Leu Ile Lys Xaa
            20                  25                  30

Met Met Ile Lys Cys Ala Xaa Xaa Xaa Asn Pro Cys Arg Pro Leu Asp
        35                  40                  45

Leu Cys Ile Glu Trp Ala Gly Arg Ile Ser Glu Glu Tyr Phe Ala Gln
    50                  55                  60

Thr Asp Glu Glu Lys Arg Gln Gly Leu Pro Val Val Met Xaa Val Phe
65                  70                  75                  80

Asp
```

(2) INFORMATION FOR SEQ ID NO:4:

(i) SEQUENCE CHARACTERISTICS:
        (A) LENGTH: 245 base pairs
        (B) TYPE: nucleic acid
        (C) STRANDEDNESS: single
        (D) TOPOLOGY: linear (vii) IMMEDIATE SOURCE:
        (A) LIBRARY: LATRNOT01
        (B) CLONE: 464655

(xi) SEQUENCE DESCRIPTION: SEQ ID NO:4:

```
CATCAACAAG CCAATGGCAG CTGAGATTGA AGGCAGCGAC TGTGAATGCA ACCCTGCTGG      60

GAAGAACTTC CCTGNAAACC AAATCCTGAT CAAANGCATG ATGATTAAGT GTGCTGANGN      120

GGNCAACCCA TGCCGACCCT GGACCTGTG CATTGAATGG GCTGGGAGGA TCTCTGAGGA       180

GTATTTTGCA CAGACTGATG AAGAGAAGAG ACAGGGACTA CCTGTGGTGA TGNCAGTGTT     240

TGACC                                                                  245
```

(2) INFORMATION FOR SEQ ID NO:5:

(i) SEQUENCE CHARACTERISTICS:
        (A) LENGTH: 713
        (B) TYPE: amino acid
        (C) STRANDEDNESS: single
        (D) TOPOLOGY: linear (vii) IMMEDIATE SOURCE:
        (A) LIBRARY: THPIPLB02
        (B) CLONE: 156196

(xi) SEQUENCE DESCRIPTION: SEQ ID NO:5:

```
Leu Ala Cys Phe Leu Asp Lys His His Asp Ile Ile Ile Ile Asp His
1               5                   10                  15
```

```
Arg Asn Pro Arg Gln Leu Asp Ala Glu Ala Leu Cys Arg Ser Ile Arg
         20                  25                  30

Ser Ser Lys Leu Ser Glu Asn Thr Val Ile Val Gly Val Val Arg Arg
         35                  40                  45

Val Asp Arg Glu Glu Leu Ser Val Met Pro Phe Ile Ser Ala Gly Phe
         50                  55                  60

Thr Arg Arg Tyr Val Glu Asn Pro Asn Ile Met Ala Cys Tyr Asn Glu
 65                  70                  75                  80

Leu Leu Gln Leu Glu Phe Gly Glu Val Arg Ser Gln Leu Lys Leu Arg
                     85                  90                  95

Ala Cys Asn Ser Val Phe Thr Ala Leu Glu Asn Ser Glu Asp Ala Ile
                    100                 105                 110

Glu Ile Thr Ser Glu Asp Arg Phe Ile Gln Tyr Ala Asn Pro Ala Phe
                115                 120                 125

Glu Thr Thr Met Gly Tyr Gln Ser Gly Glu Leu Ile Gly Lys Glu Leu
            130                 135                 140

Gly Glu Val Pro Ile Asn Glu Lys Lys Ala Asp Leu Leu Asp Thr Ile
145                 150                 155                 160

Asn Ser Cys Ile Arg Ile Gly Lys Glu Trp Gln Gly Ile Tyr Tyr Ala
                165                 170                 175

Lys Lys Lys Asn Gly Asp Asn Ile Gln Gln Asn Val Lys Ile Ile Pro
                180                 185                 190

Val Ile Gly Gln Gly Gly Lys Ile Arg His Tyr Val Ser Ile Ile Arg
                195                 200                 205

Val Cys Asn Gly Asn Asn Lys Ala Glu Lys Ile Ser Glu Cys Val Gln
            210                 215                 220

Ser Asp Thr Arg Thr Asp Asn Gln Thr Gly Lys His Lys Asp Arg Arg
225                 230                 235                 240

Lys Gly Ser Leu Asp Val Lys Ala Val Ala Ser Arg Ala Thr Glu Val
                245                 250                 255

Ser Ser Gln Arg Arg His Ser Ser Met Ala Arg Ile His Ser Met Thr
                260                 265                 270

Ile Glu Ala Pro Ile Thr Lys Val Ile Asn Val Ile Asn Ala Ala Gln
                275                 280                 285

Glu Ser Ser Pro Met Pro Val Thr Glu Ala Leu Asp Arg Val Leu Glu
            290                 295                 300

Ile Leu Arg Thr Thr Glu Leu Tyr Ser Pro Gln Phe Gly Ala Lys Asp
305                 310                 315                 320

Asp Asp Pro His Ala Asn Asp Leu Val Gly Gly Leu Met Ser Asp Gly
                325                 330                 335

Leu Arg Arg Leu Ser Gly Asn Glu Tyr Val Leu Ser Thr Lys Asn Thr
                340                 345                 350

Gln Met Val Ser Ser Asn Ile Ile Thr Pro Ile Ser Leu Asp Asp Val
                355                 360                 365

Pro Pro Arg Ile Ala Arg Ala Met Glu Asn Glu Glu Tyr Trp Asp Phe
            370                 375                 380

Asp Ile Phe Glu Leu Glu Ala Ala Thr His Asn Arg Pro Leu Ile Tyr
385                 390                 395                 400

Leu Gly Leu Lys Met Phe Ala Arg Phe Gly Ile Cys Glu Phe Leu His
                405                 410                 415

Cys Ser Glu Ser Thr Leu Arg Ser Trp Leu Gln Ile Ile Glu Ala Asn
                420                 425                 430

Tyr His Ser Ser Asn Pro Tyr His Asn Ser Thr His Ser Ala Asp Val
```

```
                 435                 440                 445
Leu His Ala Thr Ala Tyr Phe Leu Ser Lys Glu Arg Ile Lys Glu Thr
450                 455                 460

Leu Asp Pro Ile Asp Glu Val Ala Ala Leu Ile Ala Ala Thr Ile His
465                 470                 475                 480

Asp Val Asp His Pro Gly Arg Thr Asn Ser Phe Leu Cys Asn Ala Gly
                485                 490                 495

Ser Glu Leu Ala Ile Leu Tyr Asn Asp Thr Ala Val Leu Glu Ser His
            500                 505                 510

His Ala Ala Leu Ala Phe Gln Leu Thr Thr Gly Asp Asp Lys Cys Asn
        515                 520                 525

Ile Phe Lys Asn Met Glu Arg Asn Asp Tyr Arg Thr Leu Arg Gln Gly
    530                 535                 540

Ile Ile Asp Met Val Leu Ala Thr Glu Met Thr Lys His Phe Glu His
545                 550                 555                 560

Val Asn Lys Phe Val Asn Ser Ile Asn Lys Pro Leu Ala Thr Leu Glu
                565                 570                 575

Glu Asn Gly Glu Thr Asp Lys Asn Gln Glu Val Ile Asn Thr Met Leu
            580                 585                 590

Arg Thr Pro Glu Asn Arg Thr Leu Ile Lys Arg Met Leu Ile Lys Cys
        595                 600                 605

Ala Asp Val Ser Asn Pro Cys Arg Pro Leu Gln Tyr Cys Ile Glu Trp
610                 615                 620

Ala Ala Arg Ile Ser Glu Glu Tyr Phe Ser Gln Thr Asp Glu Glu Lys
625                 630                 635                 640

Gln Gln Gly Leu Pro Val Val Met Pro Val Phe Asp Arg Asn Thr Cys
                645                 650                 655

Ser Ile Pro Lys Ser Gln Ile Ser Phe Ile Asp Tyr Phe Ile Thr Asp
            660                 665                 670

Met Phe Asp Ala Trp Asp Ala Phe Val Asp Leu Pro Asp Leu Met Gln
        675                 680                 685

His Leu Asp Asn Asn Phe Lys Tyr Trp Lys Gly Leu Asp Glu Met Lys
    690                 695                 700

Leu Arg Asn Leu Arg Pro Pro Glu
705                 710

(2) INFORMATION FOR SEQ ID NO:6:

(i) SEQUENCE CHARACTERISTICS:
        (A) LENGTH: 3396 base pairs
        (B) TYPE: nucleic acid
        (C) STRANDEDNESS: single
        (D) TOPOLOGY: linear (vii) IMMEDIATE SOURCE:
        (A) LIBRARY: THPIPLB02
        (B) CLONE: 156196

(xi) SEQUENCE DESCRIPTION: SEQ ID NO:6:

CTTGCCTGTT TCCTGGACAA ACATCATGAC ATTATCATCA TAGACCACAG AAATCCTCGA        60

CAGCTGGATG CAGAGGCACT GTGCAGGTCT ATCAGATCAT CAAAACTCTC AGAAAACACA       120

GTTATTGTTG GTGTAGTACG CAGGGTGGAT AGAGAAGAGT TGTCCGTAAT GCCTTTCATT       180

TCTGCTGGAT TTACAAGGAG GTATGTGAAA ACCCCAACA TCATGGCCTG CTACAATGAA        240

CTGCTCCAGC TGGAGTTTGG AGAGGTGCGA TCACAACTGA AACTCAGGGC TTGTAACTCA       300

GTATTCACTG CATTAGAAAA CAGTGAAGAT GCAATTGAAA TTACAAGCGA AGACCGTTTT       360
```

```
ATACAGTATG CAAATCCTGC ATTTGAAACA ACAATGGGCT ATCAGTCAGG TGAATTAATA     420

GGGAAGGAGT TAGGAGAAGT GCCTATAAAT GAAAAAAAGG CTGACTTGCT CGATACTATA     480

AATTCATGCA TCAGGATAGG CAAGGAGTGG CAAGGAATTT ACTATGCCAA AAAGAAAAAC     540

GGAGATAATA TACAACAAAA TGTGAAGATA ATACCTGTCA TTGGACAGGG AGGAAAAATT     600

AGACACTATG TGTCCATTAT CAGAGTGTGC AATGGCAACA ATAAGGCTGA GAAAATATCC     660

GAATGTGTTC AGTCTGACAC TCGTACAGAT AATCAGACAG GCAAACATAA AGACAGGAGA     720

AAAGGCTCAC TAGACGTCAA AGCTGTTGCC TCCCGTGCAA CTGAAGTTTC CAGCCAGAGA     780

CGACACTCTT CCATGGCCCG GATACATTCC ATGACAATTG AGGCGCCCAT CACCAAGGTA     840

ATCAATGTTA TCAATGCTGC CCAGGAAAGT AGTCCCATGC CTGTGACAGA AGCCCTAGAC     900

CGTGTGCTGG AAATTCTAAG AACCACTGAG TTATATTCAC CACAGTTTGG TGCTAAAGAT     960

GATGATCCCC ATGCCAATGA CCTTGTTGGG GGCTTAATGT CTGATGGTTT GCGAAGACTA    1020

TCAGGGAATG AATATGTTCT TTCAACAAAA AACACTCAAA TGGTTTCAAG CAATATAATC    1080

ACTCCCATCT CCCTTGATGA TGTCCCACCA CGGATAGCTC GGGCCATGGA AAATGAGGAA    1140

TACTGGGACT TTGATATTTT TGAACTGGAG GCTGCCACCC ACAATAGGCC TTTGATTTAT    1200

CTTGGTCTCA AAATGTTTGC TCGCTTTGGA ATCTGTGAAT TCTTACACTG CTCCGAGTCA    1260

ACGCTAAGAT CATGGTTACA AATTATCGAA GCCAATTATC ATTCCTCCAA TCCCTACCAC    1320

AATTCTACAC ATTCTGCTGA TGTGCTTCAT GCCACTGCCT ATTTTCTCTC CAAGGAGAGG    1380

ATAAAGGAAA CTTTAGATCC AATTGATGAG GTCGCTGCAC TCATCGCAGC CACCATTCAT    1440

GATGTGGATC ACCCTGGGAG AACCAACTCC TTCCTGTGTA ATGCTGGAAG TGAGCTGGCC    1500

ATTTTGTACA ATGACACTGC TGTGCTGGAG AGCCACCATG CGGCCTTGGC CTTCCAGCTG    1560

ACCACTGGAG ATGATAAATG CAATATATTT AAAAACATGG AGAGGAATGA TTATCGGACA    1620

CTGCGCCAGG GGATTATCGA CATGGTCTTA GCCACAGAAA TGACAAAGCA CTTTGAGCAT    1680

GTCAACAAAT TTGTCAACAG CATCAACAAA CCCTTGGCAA CACTAGAAGA AAATGGGGAA    1740

ACTGATAAAA ACCAGGAAGT GATAAACACT ATGCTTAGGA CTCCAGAGAA CCGGACCCTA    1800

ATCAAACGAA TGCTGATTAA ATGTGCTGAT GTGTCCAATC CCTGCCGACC CCTGCAGTAC    1860

TGCATCGAGT GGGCTGCACG CATTTCGGAA GAATATTTTT CTCAGACTGA TGAAGAGAAG    1920

CAGCAGGGCT TACCTGTGGT GATGCCAGTG TTTGACAGAA ATACCTGCAG CATCCCCAAA    1980

TCCCAAATCT CTTTCATTGA TTACTTCATC ACAGACATGT TTGATGCTTG GGATGCCTTT    2040

GTAGACCTGC CTGATTTAAT GCAGCATCTT GACAACAACT TTAAATACTG GAAAGGACTG    2100

GACGAAATGA AGCTGCGGAA CCTCCGACCA CCTCCTGAAT AGTGGGAGAC ACCACCCAGA    2160

GCCCTGAAGC TTTGTTCCTT CGGTCATTTG GAATTCCTGA GGGCAGCCAG AGCTCCTTGG    2220

TCCTTTCAGT ACTAGGCAGA ACAGCCCCCG ATCTGCATAG CCTGTGAAAG CCCACGGGGA    2280

CATCAGTAAC CTTCTGCAGC CACCATCCAA TGCCATTACT GTCAAGTGAG ACTTGGCCAC    2340

TGTAGCCTGG GCCTGCTGCA GGAGCTCTTC AGAAAGGCAC ATGAGGACCA CGGTTTGCCT    2400

CAGTTTCTGG TAAAACACAA GGTCTGGAGT GCCCCTGCAA AGGGTATTGA TGGACTTCCT    2460

GCCAGTGACA GAGCATGTCT ATTGCAAACA ATTCTCTCAG TTACGTTCAG CACTTAAGAA    2520

CGGCTAATGG CAATAGGATC TTTAGCAACT TTTTCACATC ATAGAAGGTG CAATCGCTCA    2580

CTTGGGAACA CTACTGAGAG TGACTTCTCT TTTAAAATTG AGTAGCAGAT GAAAAATTAA    2640

AATTTGAACT TGATTATTAA TATCAATTAA AATGTTTTAT TTATTTTATT AAAAGCTCAA    2700
```

```
TATTTTCTAT GAATTCAAAA ATACTTCAGA GCCAAAGCCA ACTTCAAATA CCGTGACCAA    2760

ATTTACATGA TTCATATTCA TTATGCATTA CTTGGTATAC AGACTTATTT TCATAATGCA    2820

AATTAATAAA ATGACACTTT TACTGCACTA TAGAAATATT CATGTATGTT AAACTTTTCT    2880

GATTGAGGCT AACTGGAAAA AGCTGGGGTC GTATTCTAAG TGCTAAAGAA GGCTGCTTCT    2940

ACTGTATAGA ACCCAGGGCT CTGAAACAGC TCTAGCCGCC TAATGCACTT CACAGGTAAC    3000

TCCCCAAGGT AAAACTAGAC TCTCTTGTTG GTTCGCAAAG AAAAGTTAGG ACTTAACACT    3060

TTTTTCTAAA ATTTTATAAT TCAATTTCCA AAAGTCTACT CTATTTTATA CTGTTTCTAC    3120

AAAATATTCC TTATAAAAAC AAAGAACAAA AATTGAATAT TTAATGAATT GACATTTTAT    3180

AACCAACCTG TTTTTATCTA CGGTGGGAAT CTTTGATGCC AGAAATTTAT AAAGAGGTTC    3240

TGTATCTTCA CACCTTGAAT AAGCATAATA CCATAAAAAA TGACACTTGA CATGTCAATG    3300

TATTTGTCAT TCATTTTAA ACTCGTATTT GTGGTTTTTT TCCCAGATAA AAATGAAATT    3360

AAACCATTTC TTTTTAAGAA AAAAAAAAAA AAAAA                              3396
```

(2) INFORMATION FOR SEQ ID NO:7:

(i) SEQUENCE CHARACTERISTICS:
      (A) LENGTH: 718 amino acids
      (B) TYPE: amino acid
      (C) STRANDEDNESS: single
      (D) TOPOLOGY: linear (vii) IMMEDIATE SOURCE:
      (A) LIBRARY: LATRNOT01
      (B) CLONE: 464655

(xi) SEQUENCE DESCRIPTION: SEQ ID NO:7:

```
Ala Leu Glu Cys Phe Leu Asp Lys His His Glu Ile Ile Val Ile Asp
  1               5                  10                  15

His Arg Gln Thr Gln Asn Phe Asp Ala Glu Ala Val Cys Arg Ser Ile
             20                  25                  30

Arg Ala Thr Asn Pro Ser Glu His Thr Val Ile Leu Ala Val Val Ser
         35                  40                  45

Arg Val Ser Asp Asp His Glu Glu Ala Ser Val Leu Pro Leu Leu His
     50                  55                  60

Ala Gly Phe Asn Arg Arg Phe Met Glu Asn Ser Ser Ile Ile Ala Cys
 65                  70                  75                  80

Tyr Asn Glu Leu Ile Gln Ile Glu His Gly Glu Val Arg Ser Gln Phe
                 85                  90                  95

Lys Leu Arg Ala Cys Asn Ser Val Phe Thr Ala Leu Asp His Cys His
            100                 105                 110

Glu Ala Ile Glu Ile Thr Ser Asp Asp His Val Ile Gln Tyr Val Asn
        115                 120                 125

Pro Ala Phe Glu Arg Met Met Gly Tyr His Lys Gly Glu Leu Leu Gly
    130                 135                 140

Lys Glu Leu Ala Asp Leu Pro Lys Ser Asp Lys Asn Arg Ala Asp Leu
145                 150                 155                 160

Leu Asp Thr Ile Asn Thr Cys Ile Lys Lys Gly Lys Glu Trp Gln Gly
                165                 170                 175

Val Tyr Tyr Ala Arg Arg Lys Ser Gly Asp Ser Ile Gln Gln His Val
            180                 185                 190

Lys Ile Thr Pro Val Ile Gly Gln Gly Gly Lys Ile Arg His Phe Val
        195                 200                 205

Ser Leu Lys Lys Leu Cys Cys Thr Thr Asp Asn Asn Lys Gln Ile His
```

-continued

```
        210                 215                 220
Lys Ile His Arg Asp Ser Gly Asp Asn Ser Gln Thr Glu Pro His Ser
225                 230                 235                 240

Phe Arg Tyr Lys Asn Arg Arg Lys Glu Ser Ile Asp Val Lys Ser Ile
                245                 250                 255

Ser Ser Arg Gly Ser Asp Ala Pro Ser Leu Gln Asn Arg Arg Tyr Pro
            260                 265                 270

Ser Met Ala Arg Ile His Ser Met Thr Ile Glu Ala Pro Ile Thr Lys
        275                 280                 285

Val Ile Asn Ile Ile Asn Ala Gln Glu Asn Ser Pro Val Thr Val
    290                 295                 300

Ala Glu Ala Leu Asp Arg Val Leu Glu Ile Leu Arg Thr Thr Glu Leu
305                 310                 315                 320

Tyr Ser Pro Gln Leu Gly Thr Lys Asp Glu Asp Pro His Thr Ser Asp
                325                 330                 335

Leu Val Gly Gly Leu Met Thr Asp Gly Leu Arg Arg Leu Ser Gly Asn
            340                 345                 350

Glu Tyr Val Phe Thr Lys Asn Val His Gln Ser His Ser His Leu Ala
        355                 360                 365

Met Pro Ile Thr Ile Asn Asp Val Pro Pro Cys Ile Ser Gln Leu Leu
    370                 375                 380

Asp Asn Glu Glu Ser Trp Asp Phe Asn Ile Phe Glu Leu Glu Ala Ile
385                 390                 395                 400

Thr His Lys Arg Pro Leu Val Tyr Leu Gly Leu Lys Val Phe Ser Arg
                405                 410                 415

Phe Gly Val Cys Glu Phe Leu Asn Cys Ser Glu Thr Thr Leu Arg Ala
            420                 425                 430

Trp Phe Gln Val Ile Glu Ala Asn Tyr His Ser Ser Asn Ala Tyr His
        435                 440                 445

Asn Ser Thr His Ala Ala Asp Val Leu His Ala Thr Ala Phe Phe Leu
    450                 455                 460

Gly Lys Glu Arg Val Lys Gly Ser Leu Asp Gln Leu Asp Glu Val Ala
465                 470                 475                 480

Ala Leu Ile Ala Ala Thr Val His Asp Val Asp His Pro Gly Arg Thr
                485                 490                 495

Asn Ser Phe Leu Cys Asn Ala Gly Ser Glu Leu Ala Val Leu Tyr Asn
            500                 505                 510

Asp Thr Ala Val Leu Glu Ser His His Thr Ala Leu Ala Phe Gln Leu
        515                 520                 525

Thr Val Lys Asp Thr Lys Cys Asn Ile Phe Lys Asn Ile Asp Arg Asn
    530                 535                 540

His Tyr Arg Thr Leu Arg Gln Ala Ile Ile Asp Met Val Leu Ala Thr
545                 550                 555                 560

Glu Met Thr Lys His Phe Glu His Val Asn Lys Phe Val Asn Ser Ile
                565                 570                 575

Asn Lys Pro Met Ala Ala Glu Ile Glu Gly Ser Asp Cys Glu Cys Asn
            580                 585                 590

Pro Ala Gly Lys Asn Phe Pro Glu Asn Gln Ile Leu Ile Lys Arg Met
        595                 600                 605

Met Ile Lys Cys Ala Asp Val Ala Asn Pro Cys Arg Pro Leu Asp Leu
    610                 615                 620

Cys Ile Glu Trp Ala Gly Arg Ile Ser Glu Glu Tyr Phe Ala Gln Thr
625                 630                 635                 640
```

```
Asp Glu Glu Lys Arg Gln Gly Leu Pro Val Val Met Pro Val Phe Asp
                645                 650                 655

Arg Asn Thr Cys Ser Ile Pro Lys Ser Gln Ile Ser Phe Ile Asp Tyr
            660                 665                 670

Phe Ile Thr Asp Met Phe Asp Ala Trp Asp Ala Phe Ala His Leu Pro
        675                 680                 685

Ala Leu Met Gln His Leu Ala Asp Asn Tyr Lys His Trp Lys Thr Leu
    690                 695                 700

Asp Asp Leu Lys Cys Lys Ser Leu Arg Leu Pro Ser Asp Ser
705             710                 715

(2) INFORMATION FOR SEQ ID NO:8:

(i) SEQUENCE CHARACTERISTICS:
        (A) LENGTH: 2657 base pairs
        (B) TYPE: nucleic acid
        (C) STRANDEDNESS: single
        (D) TOPOLOGY: linear (vii) IMMEDIATE SOURCE:
        (A) LIBRARY: LATRNOT01
        (B) CLONE: 464655

(xi) SEQUENCE DESCRIPTION: SEQ ID NO:8:
```

| | | | | | |
|---|---|---|---|---|---|
| GCCCTTGAAT | GCTTTCTTGA | TAAGCATCAT | GAAATTATTG | TAATTGATCA | TAGACAAACT | 60 |
| CAGAACTTCG | ATGCAGAAGC | AGTGTGCAGG | TCGATCCGGG | CCACAAATCC | CTCCGAGCAC | 120 |
| ACGGTGATCC | TCGCAGTGGT | TTCGCGAGTA | TCGGATGACC | ATGAAGAGGC | GTCAGTCCTT | 180 |
| CCTCTTCTCC | ACGCAGGCTT | CAACAGGAGA | TTTATGGAGA | ATAGCAGCAT | AATTGCTTGC | 240 |
| TATAATGAAC | TGATTCAAAT | AGAACATGGG | GAAGTTCGCT | CCCAGTTCAA | ATTACGGGCC | 300 |
| TGTAATTCAG | TGTTTACAGC | ATTAGATCAC | TGTCATGAAG | CCATAGAAAT | AACAAGCGAT | 360 |
| GACCACGTGA | TTCAGTATGT | CAACCCAGCC | TTCGAAAGGA | TGATGGGCTA | CCACAAAGGT | 420 |
| GAGCTCCTGG | GAAAAGAACT | CGCTGATCTG | CCCAAAAGCG | ATAAGAACCG | GCAGACCTT | 480 |
| CTCGACACCA | TCAATACATG | CATCAAGAAG | GGAAAGGAGT | GGCAGGGGGT | TTACTATGCC | 540 |
| AGACGGAAAT | CCGGGGACAG | CATCCAACAG | CACGTGAAGA | TCACCCCAGT | GATTGGCCAA | 600 |
| GGAGGGAAAA | TTAGGCATTT | TGTCTCGCTC | AAGAAACTGT | GTTGTACCAC | TGACAATAAT | 660 |
| AAGCAGATTC | ACAAGATTCA | TCGTGATTCA | GGAGACAATT | CTCAGACAGA | GCCTCATTCA | 720 |
| TTCAGATATA | AGAACAGGAG | GAAAGAGTCC | ATTGACGTGA | AATCGATATC | ATCTCGAGGC | 780 |
| AGTGATGCAC | CAAGCCTGCA | GAATCGTCGC | TATCCGTCCA | TGGCGAGGAT | CCACTCCATG | 840 |
| ACCATCGAGG | CTCCCATCAC | AAAGGTTATA | AATATAATCA | ATGCAGCCCA | AGAAAACAGC | 900 |
| CCAGTCACAG | TAGCGGAAGC | CTTGGACAGA | GTTCTAGAGA | TTTTACGGAC | CACAGAACTG | 960 |
| TACTCCCCTC | AGCTGGGTAC | CAAAGATGAA | GATCCCCACA | CCAGTGATCT | TGTTGGAGGC | 1020 |
| CTGATGACTG | ACGGCTTGAG | AAGACTGTCA | GGAAACGAGT | ATGTGTTTAC | TAAGAATGTG | 1080 |
| CACCAGAGTC | ACAGTCACCT | TGCAATGCCA | ATAACCATCA | TGATGTTCC | CCCTTGTATC | 1140 |
| TCTCAATTAC | TTGATAATGA | GGAGAGTTGG | GACTTCAACA | TCTTTGAATT | GGAAGCCATT | 1200 |
| ACGCATAAAA | GGCCATTGGT | TTATCTGGGC | TTAAAGGTCT | TCTCTCGGTT | TGGAGTATGT | 1260 |
| GAGTTTTTAA | ACTGTTCTGA | AACCACTCTT | CGGGCCTGGT | TCCAAGTGAT | CGAAGCCAAC | 1320 |
| TACCACTCTT | CCAATGCCTA | CCACAACTCC | ACCCATGCTG | CCGACGTCCT | GCACGCCACC | 1380 |
| GCTTTCTTTC | TTGGAAAGGA | AAGAGTAAAG | GGAAGCCTCG | ATCAGTTGGA | TGAGGTGGCA | 1440 |

```
GCCCTCATTG CTGCCACAGT CCATGACGTG GATCACCCGG GAAGGACCAA CTCTTTCCTC    1500

TGCAATGCAG GCAGTGAGCT TGCTGTGCTT TACAATGACA CTGCTGTTCT GGAGAGTCAC    1560

CACACCGCCC TGGCCTTCCA GCTCACGGTC AAGGACACCA AATGCAACAT TTTCAAGAAT    1620

ATTGACAGGA ACCATTATCG AACGCTGCGC CAGGCTATTA TTGACATGGT TTTGGCAACA    1680

GAGATGACAA AACACTTTGA ACATGTGAAT AAGTTTGTGA ACAGCATCAA CAAGCCAATG    1740

GCAGCTGAGA TTGAAGGCAG CGACTGTGAA TGCAACCCTG CTGGGAAGAA CTTCCCTGAA    1800

AACCAAATCC TGATCAAACG CATGATGATT AAGTGTGCTG ACGTGGCCAA CCCATGCCGC    1860

CCCTTGGACC TGTGCATTGA ATGGGCTGGG AGGATCTCTG AGGAGTATTT TGCACAGACT    1920

GATGAAGAGA AGACAGGG ACTACCTGTG GTGATGCCAG TGTTTGACCG GAATACCTGT      1980

AGCATCCCCA AGTCTCAGAT CTCTTTCATT GACTACTTCA TAACAGACAT GTTTGATGCT    2040

TGGGATGCCT TTGCACATCT GCCAGCCCTG ATGCAACATT TGGCTGACAA CTACAAACAC    2100

TGGAAGACAC TAGATGACCT AAAGTGCAAA AGTTTGAGGC TTCCATCTGA CAGCTAAAGC    2160

CAAGCCACAG AGGGGCCTC TTGACCGACA AAGGACACTG TGAATCACAG TAGCGTAAAC     2220

GAGAGGCCTT CCTTTCTAAT GACAATGACA GGTATTGGTG AAGGAGCTAA TGTTTAATAT    2280

TTGACCTTGA ATCATTCAAG TCCCCAAATT TCATTCTTAG AAAGTTATGT TCCATGAAGA    2340

AAAATATATG TTCTTTTGAA TACTTAATGA CAGAACAAAT ACTTGGCAAA CTCCTTTGCT    2400

CTGCTGTCAT CCTGTGTACC CTTGTCAATC CATGGAGCTG GTTCACTGTA ACTAGCAGGC    2460

CACAGGAAGC AAAGCCTTGG TGCCTGTGAG CTCATCTCCC AGGATGGTGA CTAAGTAGCT    2520

TAGCTAGTGA TCAGCTCATC CTTTACCATA AAAGTCATCA TTGCTGTTTA GCTTGACTGT    2580

TTTCCTCAAG AACATCGATC TGAAGGATTC ATAAGGAGCT TATCTGAACA GATTTATCTA    2640

AAAAAAAAAA AAAAAAA                                                  2657

(2) INFORMATION FOR SEQ ID NO:9:

(i) SEQUENCE CHARACTERISTICS:
        (A) LENGTH: 610 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1705952

(xi) SEQUENCE DESCRIPTION: SEQ ID NO:9:

Met Pro Leu Val Asp Phe Phe Cys Glu Thr Cys Ser Lys Pro Trp Leu
 1               5                  10                  15

Val Gly Trp Trp Asp Gln Phe Lys Arg Met Leu Asn Arg Glu Leu Thr
            20                  25                  30

His Leu Ser Glu Met Ser Arg Ser Gly Asn Gln Val Ser Glu Tyr Ile
        35                  40                  45

Ser Asn Thr Phe Leu Asp Lys Gln Asn Glu Val Glu Ile Pro Ser Pro
    50                  55                  60

Thr Pro Arg Gln Arg Ala Phe Gln Gln Pro Pro Ser Val Leu Arg
65                  70                  75                  80

Gln Ser Gln Pro Met Ser Gln Ile Thr Gly Leu Lys Lys Leu Val His
                85                  90                  95

Thr Gly Ser Leu Asn Thr Asn Val Pro Arg Phe Gly Val Lys Thr Asp
            100                 105                 110

Gln Glu Asp Leu Leu Ala Gln Glu Leu Glu Asn Leu Ser Lys Trp Gly
```

```
            115                 120                 125
Leu Asn Ile Phe Cys Val Ser Glu Tyr Ala Gly Gly Arg Ser Leu Ser
        130                 135                 140
Cys Ile Met Tyr Thr Ile Phe Gln Glu Arg Asp Leu Leu Lys Lys Phe
145                 150                 155                 160
His Ile Pro Val Asp Thr Met Met Tyr Met Leu Thr Leu Glu Asp
                165                 170                 175
His Tyr His Ala Asp Val Ala Tyr His Asn Ser Leu His Ala Ala Asp
                180                 185                 190
Val Leu Gln Ser Thr His Val Leu Leu Ala Thr Pro Ala Leu Asp Ala
            195                 200                 205
Val Phe Thr Asp Leu Glu Ile Leu Ala Ala Leu Phe Ala Ala Ala Ile
210                 215                 220
His Asp Val Asp His Pro Gly Val Ser Asn Gln Phe Leu Ile Asn Thr
225                 230                 235                 240
Asn Ser Glu Leu Ala Leu Met Tyr Asn Asp Glu Ser Val Leu Glu Asn
                245                 250                 255
His His Leu Ala Val Gly Phe Lys Leu Leu Gln Glu Glu Asn Cys Asp
                260                 265                 270
Ile Phe Gln Asn Leu Ser Lys Arg Gln Arg Gln Ser Leu Arg Lys Met
            275                 280                 285
Val Ile Asp Met Val Leu Ala Thr Asp Met Ser Lys His Met Thr Leu
        290                 295                 300
Leu Ala Asp Leu Lys Thr Met Val Glu Thr Lys Lys Val Thr Ser Ser
305                 310                 315                 320
Gly Val Leu Leu Leu Asp Asn Tyr Ser Asp Arg Ile Gln Val Leu Arg
                325                 330                 335
Asn Met Val His Cys Ala Asp Leu Ser Asn Pro Thr Lys Pro Leu Glu
                340                 345                 350
Leu Tyr Arg Gln Trp Thr Asp Arg Ile Met Ala Glu Phe Phe Gln Gln
            355                 360                 365
Gly Asp Arg Glu Arg Glu Arg Gly Met Glu Ile Ser Pro Met Cys Asp
        370                 375                 380
Lys His Thr Ala Ser Val Glu Lys Ser Gln Val Gly Phe Ile Asp Tyr
385                 390                 395                 400
Ile Val His Pro Leu Trp Glu Thr Trp Ala Asp Leu Val His Pro Asp
                405                 410                 415
Ala Gln Asp Ile Leu Asp Thr Leu Glu Asp Asn Arg Asp Trp Tyr His
                420                 425                 430
Ser Ala Ile Arg Gln Ser Pro Ser Pro Pro Leu Glu Glu Pro Gly
            435                 440                 445
Gly Leu Gly His Pro Ser Leu Pro Asp Lys Phe Gln Phe Glu Leu Thr
        450                 455                 460
Leu Glu Glu Glu Glu Glu Asp Ser Leu Glu Val Pro Gly Leu Pro
465                 470                 475                 480
Thr Thr Glu Glu Thr Phe Leu Ala Ala Glu Asp Ala Arg Ala Gln Ala
                485                 490                 495
Val Asp Trp Ser Lys Val Lys Gly Pro Ser Thr Thr Val Val Glu Val
                500                 505                 510
Ala Glu Arg Leu Lys Gln Glu Thr Ala Ser Ala Tyr Gly Ala Pro Gln
            515                 520                 525
Glu Ser Met Glu Ala Val Gly Cys Ser Phe Ser Pro Gly Thr Pro Ile
        530                 535                 540
```

-continued

```
Leu Pro Asp Val Arg Thr Leu Ser Ser Ser Glu Glu Ala Pro Gly Leu
545                 550                 555                 560

Leu Gly Leu Pro Ser Thr Ala Ala Glu Val Glu Ala Pro Arg Asp His
            565                 570                 575

Leu Ala Ala Thr Arg Ala Cys Ser Ala Cys Ser Gly Thr Ser Gly Asp
                580                 585                 590

Asn Ser Ala Ile Ile Ser Ala Pro Gly Arg Trp Gly Ser Gly Gly Asp
        595                 600                 605

Pro Ala
    610
```

CYCLIC NUCLEOTIDE PHOSPHODIESTERASES

This application is a divisional application of U.S. Ser. No. 08/974,565, filed Nov. 19 1997, U.S. Pat. No. 5,932,423.

FIELD OF THE INVENTION

This invention relates to the nucleic acid and amino acid sequences of cyclic nucleotide phosphodiesterases and to the use of these sequences in the diagnosis, prevention, and treatment of cancer and immune and neuronal disorders.

BACKGROUND OF THE INVENTION

Cyclic nucleotides (cAMP and cGMP) function as intracellular second messengers to transduce a variety of extracellular signals, including hormones, light, and neurotransmitters. Cyclic nucleotide phosphodiesterases (PDEs) degrade cyclic nucleotides to the corresponding monophosphates, thereby regulating the intracellular concentrations of cyclic nucleotides and their effects on signal transduction. At least seven families of mammalian PDEs have been identified based on substrate specificity and affinity, sensitivity to cofactors, and sensitivity to inhibitory drugs (Beavo, J. A. (1995) Physiological Reviews 75: 725–48). Most of these families contain distinct genes; many of which are expressed in different tissues as alternative splice variants. Within families, there are multiple isozymes and multiple splice variants of those isozymes. The existence of multiple PDE families, isozymes, and splice variants presents an opportunity for regulation of cyclic nucleotide levels and functions.

Type 1 PDEs (PDE1s) are $Ca^{2+}$/calmodulin dependent, are reported to contain three different genes, each of which appears to have at least two different splice variants, and have been found in the lung, heart, and brain. Some of the calmodulin-dependent PDEs are regulated in vitro by phosphorylation/dephosphorylation. Phosphorylation of PDE1 decreases the affinity of the enzyme for calmodulin, decreases PDE activity, and increases steady state levels of cAMP. PDE2s are cGMP stimulated PDEs that are localized in the brain and that are thought to mediate the effects of cAMP on catecholamine secretion. PDE3s are one of the major families of PDEs present in vascular smooth muscle. PDE3s are inhibited by cGMP, have high specificity for cAMP as a substrate, and play a role in cardiac function. One isozyme of PDE3 is regulated by one or more insulin-dependent kinases. PDE4s are the predominant isoenzymes in most inflammatory cells, and some PDE4s are activated by cAMP-dependent phosphorylation. PDE5s are thought to be cGMP specific, but they may also affect cAMP function. High levels of PDE5s are found in most smooth muscle preparations, in platelets, and in the kidney. PDE6s play a role in vision and are regulated by light and cGMP. The PDE7 class has only one known member. PDE7 is cAMP specific and is most closely related to PDE4, although it is not inhibited by rolipram, a specific inhibitor of PDE4. A complete listing of PDE families 1, 2, 3, 4, 5, 6, and 7; their localization and their physiological roles is given in Beavo, supra.

PDEs are composed of a catalytic domain of ~270 amino acid, an N-terminal regulatory domain responsible for binding cofactors, and, in some cases, a C-terminal domain of unknown function. A conserved motif, HDXXHXGXXN (SEQ ID NO:17), has been identified in the catalytic domain of all PDEs. PDE families display approximately 30% amino acid identity within this catalytic domain. While within the same family, isozymes typically display about 85–95% identity in this region (e.g. PDE4A vs PDE4B). Furthermore, within a family there is extensive similarity (>60%) outside the catalytic domain, while across families, there is little or no sequence similarity.

Many functions of immune and inflammatory responses are inhibited by agents that increase intracellular levels of cAMP (Verghese, M. W. et al. (1995) Mol Pharmacol 47:1164–1171). A variety of diseases have been attributed to increased PDE activity and associated with decreased levels of cyclic nucleotides. A form of diabetes insipidus in the mouse has been associated with increased PDE4 activity, and an increase in low-$K_m$ cAMP PDE activity has been reported in leukocytes of atopic patients. Defects in PDEs have also been associated with retinal disease. Retinal degeneration in the rd mouse, autosomal recessive retinitis pigmentoss in humans, and rod/cone dysplasia 1 in Irish Setter dogs have been attributed to mutations in the PDE6B gene. PDE3 has been associated with cardiac disease.

Many inhibitors of PDEs have been identified and have undergone clinical evaluation. PDE3 inhibitors are being developed as antithrombotic agents, antihypertensive agents, and cardiotonic agents useful in the treatment of congestive heart failure. Rolipram, a PDE4 inhibitor, has been used in the treatment of depression, and other inhibitors of PDE4 are undergoing evaluation as anti-inflammatory agents. Rolipram has also been shown to inhibit lipopolysaccharide (LPS) induced TNF-alpha, which has been shown to enhance HIV-1 replication in vitro. Therefore, rolipram may inhibit HIV-1 replication (Angel, J. B. et al. (1995) AIDS 9:1137–44). Additionally, rolipram, based on its ability to suppress the production of cytokines, such as TNF alpha and beta and interferon gamma, has been shown to be effective in the treatment of encephalomyelitis. Rolipram may also be effective in treating tardive dyskinesia and was effective in treating multiple sclerosis in an experimental animal model (Sommer, N. et al., (1995) Nat. Med. 1:244–248; Sasaki, H. et al. (1995) Eur. J. Pharmacol 282:71–76).

Theophylline is a nonspecific PDE inhibitor used in the treatment of bronchial asthma and other respiratory diseases. Theophylline is believed to act on airway smooth muscle function and in an anti-inflammatory or immunomodulatory capacity in the treatment of respiratory diseases (Banner, K. H. and Page, C. P. (1995) Eur. Respir. J. 8:996–1000). Pentoxifylline is another nonspecific PDE inhibitor used in the treatment of intermittent claudication and diabetes-induced peripheral vascular disease. Pentoxifylline is also known to block TNF-alpha production and may inhibit HIV-1 replication (Angel et al., supra).

PDEs have also been reported to effect cellular proliferation of a variety of cell types and have been implicated in various cancers. Bang et al. (1994; Proc Natl Acad Sci USA 91:5330–5334) reported that growth of prostate carcinoma cell line, DU 145 and LNCap was inhibited by delivery of cAMP derivatives and phosphodiesterase inhibitors. Bang also observed a permanent conversion in phenotype from epithelial to neuronal morphology. Others have suggested that PDE inhibitors have the potential to regulate mesangial cell proliferation and lymphocyte proliferation (Matousovic, K. et al. (1995) J. Clin. Invest 96:401–410; Joulain, C. et al. (1995) J. Lipid Mediat. Cell Signal. 11:63–79, respectively). Finally, Deonarain et al. describe a cancer treatment that involves intracellular delivery of phosphodiesterases to particular cellular compartments or tumors and that results in cell death (Deonarain, M. P. et al. (1994) Br. J.Cancer 70:786–94).

The discovery of new cyclic nucleotide phosphodiesterases and the polynucleotides encoding them satisfies a need in the art by providing new compositions which are useful in the diagnosis, prevention, and treatment of cancer and immune and neuronal disorders.

SUMMARY OF THE INVENTION

The invention features substantially purified polypeptides, cyclic nucleotide phosphodiesterases, referred to collectively as "PDE8" and individually as "PDE8A," "PDE8A(E)" (PDE8A extended), "PDE8B," and "PDE8B (E)" (PDE8B extended). In one aspect, the invention provides a substantially purified polypeptide, PDE8, comprising an amino acid sequence selected from the group consisting of SEQ ID NO:1, SEQ ID NO:3, SEQ ID NO:5, SEQ ID NO:7, a fragment of SEQ ID NO:1, a fragment of SEQ ID NO:3, a fragment of SEQ ID NO:5, and a fragment of SEQ ID NO:7.

The invention further provides a substantially purified variant of PDE8 having at least 90% amino acid identity to the amino acid sequences of SEQ ID NO:1, SEQ ID NO:3, SEQ ID NO:5, or SEQ ID NO:7, a fragment of SEQ ID NO:1, a fragment of SEQ ID NO:3, a fragment of SEQ ID NO:5, or a fragment of SEQ ID NO:7. The invention also provides an isolated and purified polynucleotide sequence encoding the polypeptide comprising any of the amino acid sequences described above. The invention also includes an isolated and purified polynucleotide variant having at least 90% polynucleotide identity to the polynucleotide sequence encoding the polypeptide comprising these amino acid sequences.

Additionally, the invention provides a composition comprising a polynucleotide sequence encoding the polypeptide comprising the amino acid sequence of SEQ ID NO:1, SEQ ID NO:3, SEQ ID NO:5, SEQ ID NO:7, a fragment of SEQ ID NO:1, a fragment of SEQ ID NO:3, a fragment of SEQ ID NO:5, or a fragment of SEQ ID NO:7. The invention further provides an isolated and purified polynucleotide sequence which hybridizes under stringent conditions to one of these polynucleotide sequences, as well as an isolated and purified polynucleotide sequence which is complementary to one of these polynucleotide sequences.

The invention also provides an isolated and purified polynucleotide sequence comprising a polynucleotide sequence selected from the group consisting of SEQ ID NO:2, SEQ ID NO:4, SEQ ID NO:6, SEQ ID NO:8, a fragment of SEQ ID NO:2, a fragment of SEQ ID NO:4, a fragment of SEQ ID NO:6, and a fragment of SEQ ID NO:8. The invention further provides an isolated and purified polynucleotide variant having at least 90% polynucleotide identity to one of these polynucleotide sequences, as well as an isolated and purified polynucleotide sequence which is complementary to one of these polynucleotide sequences.

The invention further provides an expression vector containing at least a fragment of any of the claimed polynucleotide sequences. In another aspect, the expression vector containing the polynucleotide sequence is contained within a host cell.

The invention also provides a method for producing a polypeptide comprising the amino acid sequence of SEQ ID NO:1, SEQ ID NO:3, SEQ ID NO:5, SEQ ID NO:7, a fragment of SEQ ID NO:1, a fragment of SEQ ID NO:3, a fragment of SEQ ID NO:5, or a fragment of SEQ ID NO:7, the method comprising the steps of: (a) culturing the host cell containing an expression vector containing at least a fragment of a polynucleotide sequence encoding PDE8 under conditions suitable for the expression of the polypeptide; and (b) recovering the polypeptide from the host cell culture.

The invention also provides a pharmaceutical composition comprising a substantially purified PDE8 having the amino acid sequence of SEQ ID NO:1, SEQ ID NO:3, SEQ ID NO:5, SEQ ID NO:7, a fragment of SEQ ID NO:1, a fragment of SEQ ID NO:3, a fragment of SEQ ID NO:5, or a fragment of SEQ ID NO:7 in conjunction with a suitable pharmaceutical carrier.

The invention further includes a purified antibody which binds to a polypeptide comprising the amino acid sequence of SEQ ID NO:1, SEQ ID NO:3, SEQ ID NO:5, SEQ ID NO:7, a fragment of SEQ ID NO:1, a fragment of SEQ ID NO:3, a fragment of SEQ ID NO:5, or a fragment of SEQ ID NO:7, as well as a purified agonist and a purified antagonist to the polypeptide.

The invention also provides a method for treating or preventing a cancer, the method comprising administering to a subject in need of such treatment an effective amount of an antagonist of PDE8.

The invention also provides a method for treating or preventing an inmmune disorder, the method comprising administering to a subject in need of such treatment an effective amount of an antagonist of PDE8.

The invention also provides a method for treating or preventing a neuronal disorder, the method comprising administering to a subject in need of such treatment an effective amount of an antagonist of PDE8.

The invention also provides a method for detecting a polynucleotide encoding PDE8 in a biological sample containing nucleic acids, the method comprising the steps of: (a) hybridizing the complement of the polynucleotide sequence which encodes the polypeptide comprising SEQ ID NO:1, SEQ ID NO:3, SEQ ID NO:5, SEQ ID NO:7, a fragment of SEQ ID NO:1, a fragment of SEQ ID NO:3, a fragment of SEQ ID NO:5, or a fragment of SEQ ID NO:7 to at least one of the nucleic acids of the biological sample, thereby forming a hybridization complex; and (b) detecting the hybridization complex, wherein the presence of the hybridization complex indicates the presence of a polynucleotide encoding PDE8 in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of PDE8A.

FIG. 2 shows the amino acid sequence (SEQ ID NO:3) and nucleic acid sequence (SEQ ID NO:4) of PDE8B.

FIGS. 3A, 3B, 3C, 3D, 3E, 3F, 3G, 3H, and 3I show the amino acid sequence (SEQ ID NO:5) and nucleic acid sequence (SEQ ID NO:6) of PDE8A(E).

FIGS. 4A, 4B, 4C, 4D, 4E, 4F, and 4G show the amino acid sequence (SEQ ID NO:7) and nucleic acid sequence (SEQ ID NO:8) of PDE8B(E).

The alignments were produced using MacDNASIS PRO software (Hitachi Software Engineering Co. Ltd. San Francisco, Calif.).

FIGS. 5A, 5B, 5C, 5D, 5E, and 5F show the amino acid sequence alignments among PDE8A (SEQ ID NO:1), PDE8B (SEQ ID NO:3), PDE8A(E) (SEQ ID NO:5), PDE8B(E) (SEQ ID NO:7), and rat PDE4A(GI 1705952; SEQ ID NO:9)), produced using the multisequence alignment program of LASERGENE software (DNASTAR Inc. Madison Wis.).

Figure 6:
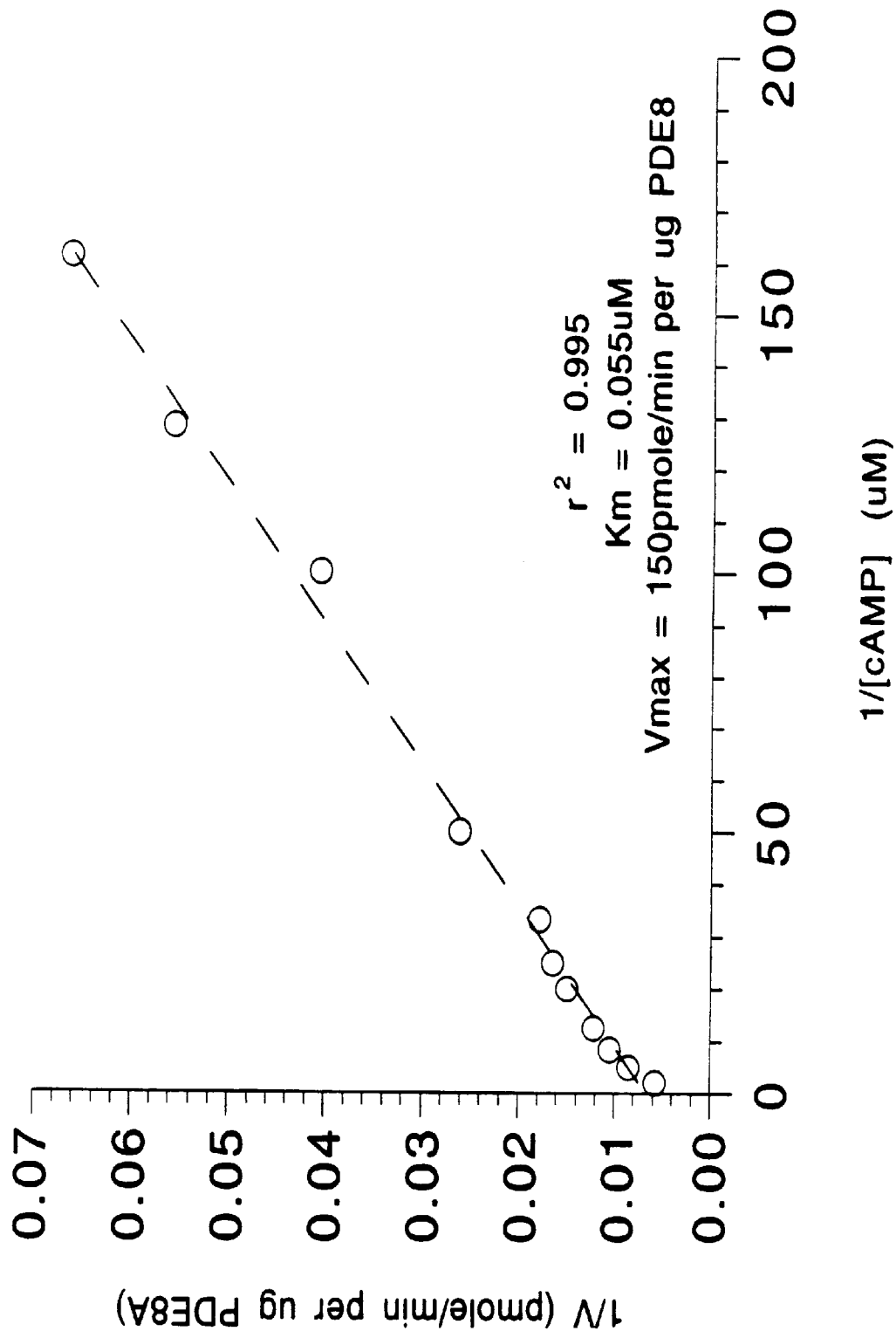

FIG. 6 shows the double-reciprocal, Lineweaver-Burke plot for the activity of PDE8A(E) using cAMP as a substrate; the positive X axis reflects the recriprocal of the substrate (cAMP) concentration (1/S), and the positive Y axis reflects the recriprocal of the reaction velocity (1/V). Lineweaver-Burke analysis was performed according to Segal, I. H. (*Enzyme Kinetics* (1995) pp. 214–245, John Wiley and Sons, New York, N.Y.)

Figure 7:
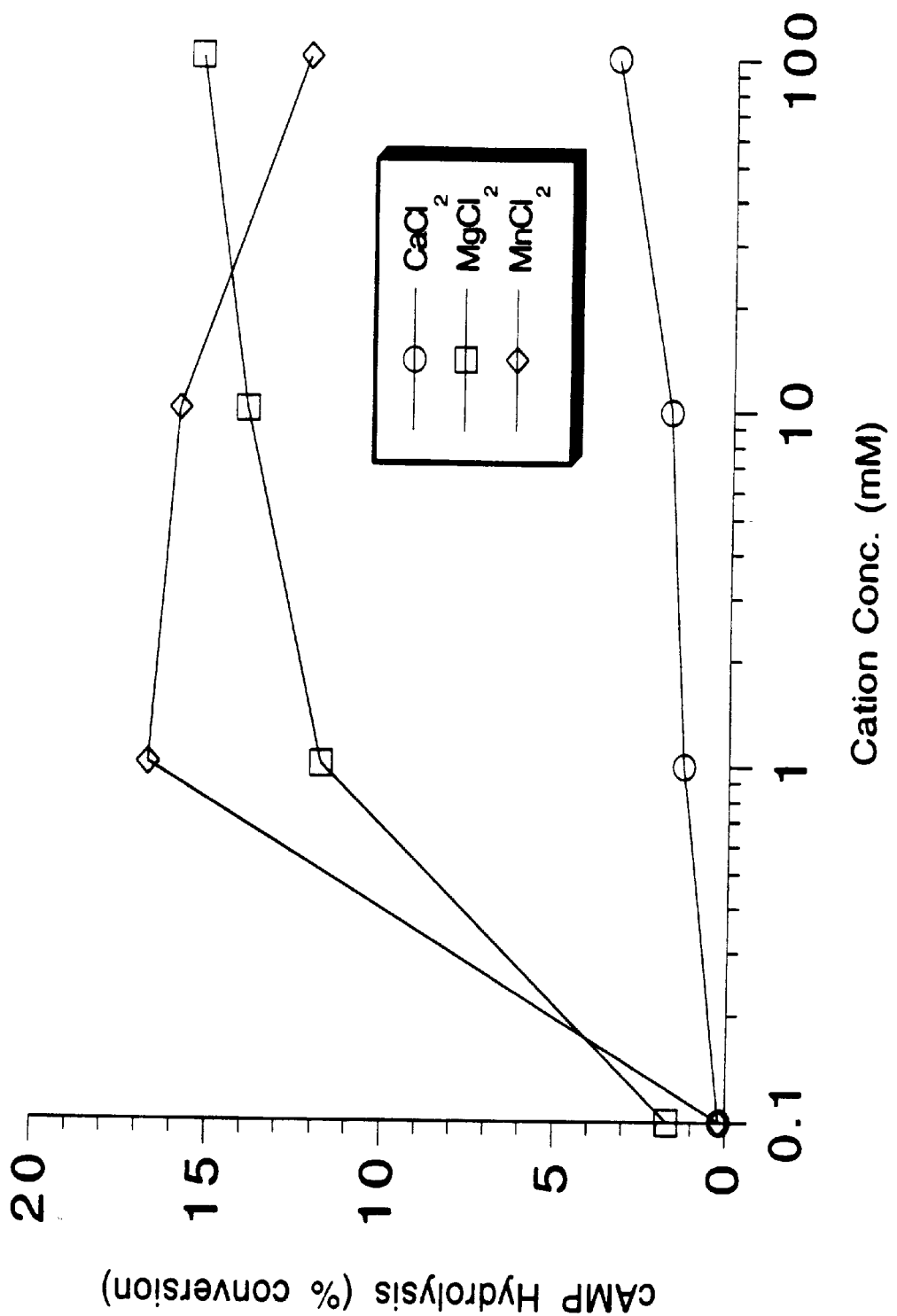

FIG. 7 shows the dependence of PDE8A(E) activity on divalent cation concentration; the positive X axis reflects cation concentration (mM), and the positive Y axis reflects the percent hydrolysis of cAMP. Divalent cations tested were calcium chloride ($CaCL_2$; circles), magnesium chloride ($MgCl_2$; squares), and manganese chloride ($MnCl_2$; diamonds).

Figure 8:
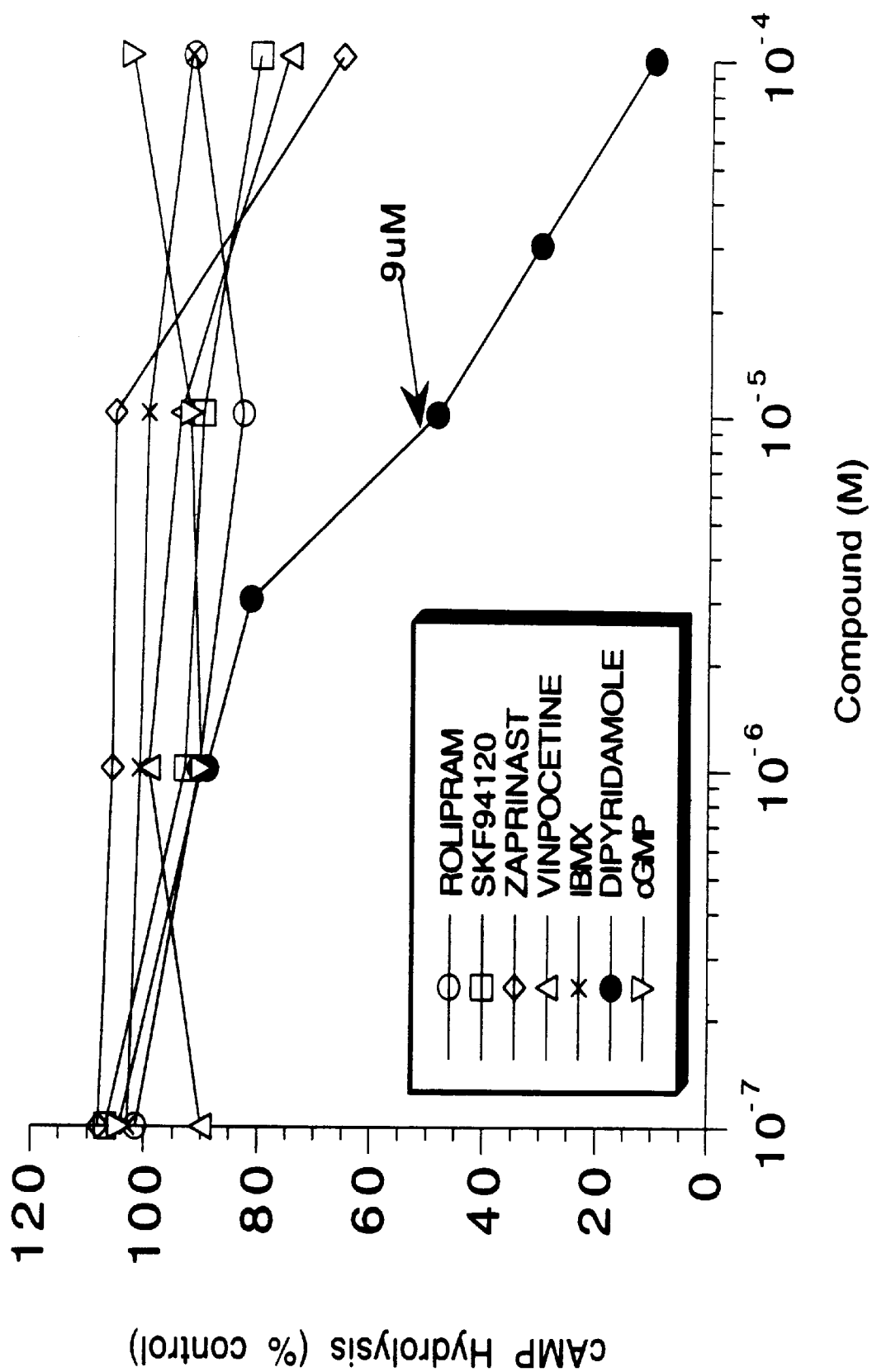

FIG. 8 shows the effect of various PDE inhibitors on the activity of PDE8A(E); the positive X axis reflects the concentration of inhibitor (M), and the positive Y axis reflects the percent inhibition of the enzyme.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

PDE8, as used herein, refers to the amino acid sequences of substantially purified PDE8 obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to PDE8, increases or prolongs the duration of the effect of PDE8. Agonists may include proteins, nucleic acids, carbohydrates, or any other molecules which bind to and modulate the effect of PDE8.

An "allele" or "allelic sequence", as used herein, is an alternative form of the gene encoding PDE8. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding PDE8, as used herein, include those with deletions, insertions, or substitutions of different nucleotides resulting in a polynucleotide that encodes the same or a functionally equivalent PDE8. Included within this definition are polymorphisms which may or may not be readily detectable using a particular oligonucleotide probe of the polynucleotide encoding PDE8, and improper or unexpected hybridization to alleles, with a locus other than the normal chromosomal locus for the polynucleotide sequence encoding PDE8. The encoded protein may also be "altered" and contain deletions, insertions, or substitutions of amino acid residues which produce a silent change and result in a functionally equivalent PDE8. Deliberate amino acid substitutions may be made on the basis of similarity in polarity, charge, solubility, hydrophobicity, hydrophilicity, and/or the amphipathic nature of the residues as long as the biological or immunological activity of PDE8 is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of PDE8 are preferably about 5 to about 15 amino acids in length and retain the biological activity or the immunological activity of PDE8. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) PCR *Primer, a Laboratory Manual*, Cold Spring Harbor Press, Plainview, N.Y.).

The term "antagonist", as used herein, refers to a molecule which, when bound to PDE8, decreases the amount or the duration of the effect of the biological or immunological activity of PDE8. Antagonists may include proteins, nucleic acids, carbohydrates, antibodies or any other molecules which decrease the effect of PDE8.

As used herein, the term "antibody" refers to intact molecules as well as fragments thereof, such as Fa, F(ab')$_2$, and Fv, which are capable of binding the epitopic determinant. Antibodies that bind PDE8 polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic PDE8, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein, refers broadly to any composition containing the given polynucleotide sequence. The composition may comprise a dry formulation or an aqueous solution. Compositions comprising polynucleotide sequences encoding PDE8 may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR Kit (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW Fragment Assembly system, GCG, Madison, Wis.). Some sequences have been both extended and assembled to produce the consensus sequence .

The term "correlates with expression of a polynucleotide", as used herein, indicates that the detection of the presence of ribonucleic acid that is similar to SEQ ID NO:2, SEQ ID NO:4, SEQ ID NO:6 by northern analysis is indicative of the presence of mRNA encoding PDE8 in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to PDE8 or the encoded PDE8. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides arranged on a substrate, such as paper, nylon or other type of membrane, filter, chip, glass slide, or any other suitable solid support.

The term "modulate", as used herein, refers to a change in the activity of PDE8. For example, modulation may cause an increase or a decrease in protein activity, binding characteristics, or any other biological, functional or immunological properties of PDE8.

"Nucleic acid sequence", as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, for example, a protein "comprising at least a portion of the amino acid sequence of SEQ ID NO:1" encompasses the full-length PDE8A and fragments thereof.

The term "sample", as used herein, is used in its broadest sense. A biological sample suspected of containing nucleic acid encoding PDE8, or fragments thereof, or PDE8 itself may comprise a bodily fluid, extract from a cell, chromosome, organelle, or membrane isolated from a cell, a cell, genomic DNA, RNA, or cDNA(in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

As used herein, the term "stringent conditions" refers to conditions which permit hybridization between polynucleotide sequences and the claimed polynucleotide sequences. Suitably stringent conditions can be defined by, for example, the concentrations of salt and/or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide or/and at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of PDE8, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

THE INVENTION

The invention is based on the discovery and extension of nucleotide sequences for a new family of human cyclic nucleotide phosphodiesterases, PDE8, the polynucleotides encoding PDE8, and the use of these compositions for the diagnosis, prevention, or treatment of cancer and immune and neuronal disorders.

Nucleic acids encoding the PDE8A of the present invention were first identified in Incyte Clone 156196 from the promonocyte cell line cDNA library (THP1PLB02) using a computer search for amino acid sequence alignments. A consensus sequence, SEQ ID NO:2, was derived from extension of the nucleic acid sequence of this clone.

In one embodiment, the invention encompasses a polypeptide comprising the amino acid sequence of SEQ ID NO:1, as shown in FIGS. 1A, 1B, 1C, 1D, 1E, and 1F. PDE8A is 449 amino acids in length and has a consensus signature sequence for cyclic nucleotide PDEs at $H_{216}$DVDHPGRTN (SEQ ID NO:1). This sequence is a part of one of two potential divalent cation binding sites conserved in PDEs, having the general structure of HXXXH $(X_{6-24})$E (SEQ ID NO:18). The first of these sites is found in the sequence $H_{176}$ - - - $H_{180}$ - - - $D_{205}$, and has $D_{205}$ as a conservative amino acid substitution for E. This substitution is found in at least one other PDE, PDE7. The second of these sites is found in the sequence $H_{216}$ - - - $H_{220}$ - - - $E_{246}$. As shown in FIGS. 5A, 5B, 5C, 5D, 5E, and 5F, PDE8A has chemical and structural homology with PDE8B (SEQ ID NO:3), PDE8A(E) (SEQ ID NO:5), PDE8B(E) (SEQ ID NO:7), and rat PDE4A (GI1705952; SEQ ID NO:9). In particular, PDE8A shares 70% identity with PDE8B in the C-terminal portion of PDE8A beginning at residue $I_{304}$. PDE8A shares 99% identity with PDE8A(E) beginning at residue $M_{265}$ in PDE8A(E). PDE8A shares 78% identity with PDE8B(E), and 29% identity with rat PDE4. The ~270 amino acid catalytic domain found in all PDEs extends approximately between residues $L_{151}$ and $W_{433}$ for PDE8A, and is 33% identical to rat PDE4A in this region. All five proteins share the two divalent cation binding sites and the consensus signature sequence, HDXXHXGXXN (SEQ ID NO:17). Electronic northern analysis using the LIFESEQ database (Inc. Pharmaceutical, Palo Alto Calif.) shows the expression of PDE8A in various libraries, at least 20% of which are immortalized or cancerous and at least 80% of which involve the immune response.

Nucleic acids encoding the PDE8B of the present invention were first identified in Incyte Clone 464655 from the atrial tissue cDNA library (LATRNOT01) using a computer search for amino acid sequence alignments. A consensus sequence, SEQ ID NO:4, was derived from extension of the nucleic acid sequence of this clone.

In another embodiment, the invention encompasses a polypeptide comprising the amino acid sequence of SEQ ID NO:3, as shown in FIG. 2. PDE8B is 81 amino acids in length. As shown in FIGS. 5A, 5B, 5C, 5D, 5E, and 5F, PDE8B shares 100% identity with the C-terminal portion of PDE8B(E) beginning at residue $L_{568}$ of the latter protein. PDE8B shares 27% identity with rat PDE4A. Electronic northern analysis shows the expression of this sequence in various libraries, at least 43% of which involve cancer, and at least 43% of which involve the brain and neural tissue.

Nucleic acids encoding the PDE8A(E) of the present invention were first identified in Incyte Clone 156196 from the promonocyte cell line cDNA library (THP1PLB02) using a computer search for amino acid sequence alignments. SEQ ID NO:6 was derived from further extension of Incyte Clone 156196.

In another embodiment, the invention encompasses a polypeptide comprising the amino acid sequence of SEQ ID NO:5, as shown in FIGS. 3A, 3B, 3C, 3D, 3E, 3F, 3H, and 3I. PDE8A(E) is 713 amino acids in length and has as consensus signature sequence for cyclic nucleotide PDEs beginning at $H_{480}$. The two divalent cation binding sites begin at residues $H_{440}$ and $H_{480}$. As shown in FIGS. 5A, 5B, 5C, 5D, 5E, and 5F, PDE8A(E) shares chemical and structural homology with the other PDE8 proteins and with rat PDE4A. In particular, the C-terminal portion of PDE8A(E) is identical (100%) with PDE8A beginning at residue $L_{568}$. PDE8A(E) shares 22% overall identity with rat PDE4 and 35% identity in the catalytic domain of PDE4.

A 1.6 kb region of PDE8A(E) encoding the C-terminal 545 amino acids was cloned into the baculovirus transfer vector pFASTBAC, expressed in sf9 cells, and a cell lysate prepared from these cells for enzyme assays. FIG. 6 shows the kinetics of enzyme activity of recombinant, purified PDE8A(E) with cAMP as a substrate. PDE8A(E) has a very high affinity for cAMP with a Km of 55 nM, and a very low affinity for cGMP (Km=124 mM, data not shown). FIG. 7 shows the dependence of PDE8A(E) on divalent cations for maximal activity with a preference for $Mn^{++}$ or $Mg^{++}$ over $Ca^{++}$. The effects of various known PDE inhibitors on the activity of PDE8A(E) are shown in FIG.8. PDE8A(E) was not inhibited by up to 100 mM of rolipram, SKF94120 (inhibitor of PDE3), zaprinast (inhibitor of PDE5), vinpocetine (inhibitor of PDE1), of IBMX (non-specific PDE inhibitor). PDE8A(E) was inhibited by dipyridamole (inhibitor of PDE5) with an $IC_{50}$ of 9 $\mu$M. Membrane-based northern analysis shows the expression of this sequence in various tissues, with the most significant expression in testis, ovary, small intestine, and colon.

Nucleic acids encoding the PDE8B(E) of the present invention were first identified in Incyte Clone 464655 from the atrial tissue cDNA library (LATRNOT01) using a computer search for amino acid sequence alignments. SEQ ID NO:8 was derived from extension and assembly of Incyte Clones 464655 (LATRNOT01) and 112633 (PITUNOT01).

In another embodiment, the invention encompasses a polypeptide comprising the amino acid sequence of SEQ ID NO:7, as shown in FIGS. 4A, 4B, 4C, 4D, 4E, 4F, and 4G. PDE8B(E) is 718 amino acids in length and has a consensus cyclic nucleotide PDE signature sequence beginning at $H_{488}$. The two divalent cation binding sites begin at residues $H_{448}$ and $H_{488}$. As shown in FIGS. 5A, 5B, 5C, 5D, 5E, and 5F, PDE8B(E) has chemical and structural homology with the other PDE8 proteins and with rat PDE4A. In particular, the C-terminal portion of PDE8B(E) is identical (100%) with PDE8B between residues $L_{576}$ and $D_{656}$ of PDE8B(E). PDE8B(E) shares 71% identity with PDE8A(E) and 22% identity with rat PDE4A.

The degree of similarity exhibited among the four PDE8 proteins (70% to 100%) is consistent with that shown between isozymes within the same family, while the degree of similarity between the four PDE8 proteins and PDE4 (22% to 29%) is consistent with that shown between isozymes of different families. PDE8A(E) is further distinguished from other known families by its specificity for cAMP and pattern of inhibition by known PDE inhibitors.

PDE8A, PDE8A(E), PDE8B, and PDE8B(E) therefore appear to constitute a new family of cyclic nucleotide phosphodiesterases designated PDE8.

The invention also encompasses PDE8 variants. A preferred PDE8 variant is one having at least 80%, and more preferably at least 90%, amino acid sequence identity to the PDE8 amino acid sequence claimed herein and which retains at least one biological, immunological or other functional characteristic or activity of PDE8. A most preferred PDE8 variant is one having at least 95% amino acid sequence identity.

The invention also encompasses polynucleotide sequences which encode PDE8. Accordingly, any nucleic acid sequence which encodes the amino acid sequence of PDE8 can be used to produce recombinant molecules which express PDE8. In a particular embodiment, the invention encompasses the polynucleotide comprising the nucleic acid sequence of SEQ ID NO:2 as shown in FIGS. 1A, 1B, 1C, 1D, 1E, and 1F. In another embodiment, the invention encompasses the polynucleotide comprising the nucleic acid sequence of SEQ ID NO:4 as shown in FIG. 2. In another embodiment, the invention encompasses the polynucleotide comprising the nucleic acid sequence of SEQ ID NO:6 as shown in FIGS. 3A 3B, 3C, 3D, 3E, 3F, 3G, 3H, and 3I. In still another embodiment, the invention encompasses the polynucleotide comprising the nucleic acid sequence of SEQ ID NO:8 as shown in FIGS. 4A, 4B, 4C, 4D, 4E, 4F, and 4G.

The invention also encompasses a variant of a polynucleotide sequence encoding PDE8. In particular, such a variant polynucleotide sequence will have at least about 80%, more preferably at least about 90%, and most preferably at least about 95% polynucleotide sequence identity to the polynucleotide sequence encoding PDE8. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 which has at least at least about 80%, more preferably at least about 90%, and most preferably at least about 95% polynucleotide sequence identity to SEQ ID NO:4. Another aspect of the invention encompasses a variant of SEQ ID NO:6 which has at least about 80%, more preferably at least about 90%, and most preferably at least about 95% polynucleotide sequence identity to SEQ ID NO:6. The invention also encompasses a polynucleotide variant of SEQ ID NO:8 having at least about 80%, more preferably at least about 90%, and most preferably at least about 95% polynucleotide sequence identity to SEQ ID NO:8.

It will be appreciated by those skilled in the art that as a result of the degeneracy of the genetic code, a multitude of nucleotide sequences encoding PDE8, some bearing minimal homology to the nucleotide sequences of any known and naturally occurring gene, may be produced. Thus, the invention contemplates each and every possible variation of nucleoticle sequence that could be made by selecting combinations based on possible codon choices. These combinations are made in accordance with the standard triplet genetic code as applied to the nucleotide sequence of naturally occurring PDE8, and all such variations are to be considered as being specifically disclosed.

Although nucleotide sequences which encode PDE8 and its variants are preferably capable of hybridizing to the nucleotide sequence of the naturally occurring PDE8 under appropriately selected conditions of stringency, it may be advantageous to produce nucleotide sequences encoding PDE8 or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PDE8 and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode PDE8 and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding PDE8 or any fragment thereof.

Also encompassed by the invention are polynucleotide sequences that are capable of hybridizing to the claimed nucleotide sequences, and in particular, those shown in SEQ ID NO:2, SEQ ID NO:4, SEQ ID NO:6, and SEQ ID NO:8, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, SEQUENASE (US Biochemical Corp, Cleveland, Ohio, Taq polymerase (Perkin Elmer), thermostable T7 polymerase (Amersham, Pharmacia Biotech, Piscataway, N.J.), or combinations of polymerases and proofreading exonucleases such as those found in the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding PDE8 may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERYINDER libraries (Clontech, Palo Alto, Calif.) to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and Sequence NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode PDE8 may be used in recombinant DNA molecules to direct expression of PDE8, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express PDE8.

As will be understood by those of skill in the art, it may be advantageous to produce PDE8-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter PDE8 encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding PDE8 may be ligated to a heterologous sequence to encode a fusion protein. For example, to screen peptide libraries for inhibitors of PDE8 activity, it may be useful to encode a chimeric PDE8 protein that can be recognized by a conmmercially available antibody. A fusion protein may also be engineered to contain a cleavage site located between the PDE8 encoding sequence and the heterologous protein sequence, so that PDE8 may be cleaved and purified away from the heterologous moiety.

In another embodiment, sequences encoding PDE8 may be synthesized, in whole or in part, using chemical methods well known in the art (see Caruthers, M. H. et al. (1980) Nucl. Acids Symp. Ser. (7) 215–223, Horn, T. et al. (1980) Nucl. Acids Symp. Ser. (7) 225–232). Alternatively, the protein itself may be produced using chemical methods to synthesize the amino acid sequence of PDE8, or a fragment thereof. For example, peptide synthesis can be performed using various solid-phase techniques (Roberge, J. Y. et al. (1995) Science 269:202–204) and automated synthesis may be achieved, for example, using the ABI431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of PDE8, or any part thereof, may be altered during direct synthesis and/or combined using chemical methods with sequences from other proteins, or any part thereof, to produce a variant polypeptide.

In order to express a biologically active PDE8, the nucleotide sequences encoding PDE8 or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding PDE8 and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding PDE8. These include, but are not limited to, microorganisms such as bacteria transformed with recombinant bacteriophage, plasmid, or cosmnid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSPORT plasmid (Life Technologies) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding PDE8, vectors based on SV40 or EBV may be used with an appropriate selectable marker.

In bacterial systems, a number of expression vectors may be selected depending upon the use intended for PDE8. For example, when large quantities of PDE8 are needed for the induction of antibodies, vectors which direct high level expression of fusion proteins that are readily purified may be used. Such vectors include, but are not limited to, the multifunctional *E. coli* cloning and expression vectors such as BLUESCRIPT phagemid (Stratagene), in which the sequence encoding PDE8 may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding PDE8 may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express PDE8. For example, a 1.6 kb region of PDE8A(E) encoding the C-terminal 545 amino acids was PCR-amplified and cloned into the baculovirus transfer vector pFASTBAC (Life Technologies, Inc., Gaithersburg, Md.), which had been modified to include a 5' FLAG tag. Recombinant virus stocks were prepared according to the manufacturer's protocol. Sf9 cells were cultured in Sf900 II Sfm serum free media (Life Technologies Inc.) at 27° C. For expression, $1 \times 10^8$ Sf9 cells were infected at a multiplicity of infection of 5 in a final volume of 50 mls. Three days post-infection, the cells were harvested and enzyme-containing lysates were prepared. To monitor expression, 1 ml each of mock-infected and PDE8A(E)-infected cell lysate was electrophoresed in a polyacrylamide gel and either silver-stained by standard methods or transferred to nitrocellulose and Western blotted with an anti-FLAG antibody (M2, Scientific Imaging System, Eastman Kodak, address) at a concentration of 2 mg/ml.

In mammalian host cells, a number of viral-based expression systems may be utilized. In cases where an adenovirus is used as an expression vector, sequences encoding PDE8 may be ligated into an adenovirus transcription/translation complex consisting of the late promoter and tripartite leader sequence. Insertion in a non-essential E1 or E3 region of the viral genome may be used to obtain a viable virus which is capable of expressing PDE8 in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding PDE8. Such signals include the ATG initiation codon and adjacent sequences. In cases where sequences encoding PDE8, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express PDE8 may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk or aprt cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, βglucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding PDE8 is inserted within a marker gene sequence, transformed cells containing sequences encoding PDE8 can be identified by the absence of marker gene function. Alternatively, a marker gene can be placed in tandem with a sequence encoding PDE8 under the control of a single promoter. Expression of the marker gene in response to induction or selection usually indicates expression of the tandem gene as well.

Alternatively, host cells which contain the nucleic acid sequence encoding PDE8 and express PDE8 may be identified by a variety of procedures known to those of skill in the art. These procedures include, but are not limited to, DNA-DNA or DNA-RNA hybridizations and protein bioassay or imnmunoassay techniques which include membrane, solution, or chip based technologies for the detection and/or quantification of nucleic acid or protein.

The presence of polynucleotide sequences encoding PDE8 can be detected by DNA-DNA or DNA-RNA hybridization or amplification using probes or fragments or fragments of polynucleotides encoding PDE8. Nucleic acid amplification based assays involve the use of oligonucleotides or oligomers based on the sequences encoding PDE8 to detect transformants containing DNA or RNA encoding PDE8.

A variety of protocols for detecting and measuring the expression of PDE8, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on PDE8 is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding PDE8 include oligolabeling, nick translation, end-labeling or PCR amplification using a labeled nucleotide. Alternatively, the sequences encoding PDE8, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Amersham Pharmacia Biotech, Promega, and US Biochemical). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding PDE8 may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode PDE8 may be designed to contain signal sequences which direct secretion of PDE8 through a prokaryotic or eukaryotic cell membrane. Other constructions may be used to join sequences encoding PDE8 to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and PDE8 may be used to facilitate purification. One such expression vector provides for expression of a fusion protein containing PDE8 and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992), Prot. Exp. Purif. 3: 263–281) while the enterokinase cleavage site provides a means for purifying PDE8 from the fusion protein. A discussion of vectors which contain fusion proteins is provided in Kroll, D. J. et al. (1993; DNA Cell Biol. 12:441–453).

In addition to recombinant production, fragments of PDE8 may be produced by direct peptide synthesis using solid-phase techniques (Meffifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of PDE8 may be chemically synthesized separately and combined using chemical methods to produce the full length molecule.

THERAPEUTICS

Chemical and structural homology exists between PDE8 and PDE4 from rat (GI1705952). In addition, PDE8 is expressed in cancer, tissues associated with inflammation and the immune response, and brain. Therefore, PDE8 appears to play a role in cancer and immnune and neuronal disorders. In particular, inhibitors of PDE have been shown to be effective in the treatment of these types of diseases and disorders.

Therefore, in one embodiment, an antagonist of PDE8 may be administered to a subject to prevent or treat a cancer. Such cancers may be, but are not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds PDE8 may be used directly as an antagonist or indirectly as a targeting or delivery mechanism for bringing a pharmaceutical agent to cells or tissue which express PDE8.

In another embodiment, a vector expressing the complement of the polynucleotide encoding PDE8 may be administered to a subject to treat or prevent a cancer including, but not limited to, the types of cancer described above.

In another embodiment, an antagonist of PDE8 may be administered to a subject to prevent or treat an immune disorder. Such disorders may include, but are not limited to, AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections; and trauma.

In another embodiment, a vector expressing the complement of the polynucleotide encoding PDE8 may be administered to a subject to treat or prevent an immune disorder including, but not limited to, those described above.

In another embodiment, an antagonist of PDE8 may be administered to a subject to prevent or treat a neuronal disorder. Such disorders may include, but are not limited to, akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder.

In another embodiment, a vector expressing the complement of the polynucleotide encoding PDE8 may be administered to a subject to treat or prevent a neuronal disorder including, but not limited to, those described above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PDE8 may be produced using methods which are generally known in the art. In particular, purified PDE8 may be used to produce antibodies or to screen libraries of pharmaceutical agents to identify those which specifically bind PDE8.

Antibodies to PDE8 may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, nice, humans, and others, may be immunized by injection with PDE8 or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecitlin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides. or fragments used to induce antibodies to PDE8 have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of PDE8 amino acids may be fused with those of another protein such as keyhole limpet hemocyanin and antibody produced against the chimeric molecule.

Monoclonal antibodies to PDE8 may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce PDE8-specific single chain antibodies. Antibodies with related specificity, but of distinct idiotypic composition, may be generated by chain shuffling from random combinatorial inmunoglobalis libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 833–3837; Winter, G. et al. (1991) Nature 349:293–299).

Antibody fragments which contain specific binding sites for PDE8 may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PDE8 and its specific antibody. A two-site, monoclonal-based immunoassay utilizing monoclonal antibodies reactive to two non-interfering PDE8 epitopes is preferred, but a competitive binding assay may also be employed (Maddox, supra).

In another embodiment of the invention, the polynucleotides encoding PDE8, or any is fragment or complement thereof, may be used for therapeutic purposes. In one aspect, the complement of the polynucleotide encoding PDE8 may be used in situations in which it would be desirable to block the transcription of the mRNA. In particular, cells may be transformed with sequences complementary to polynucleotides encoding PDE8. Thus, complementary molecules or fragments may be used to modulate PDE8 activity, or to achieve regulation of gene function. Such technology is now well known in the art, and sense or antisense oligonucleotides or larger fragments, can be designed from various locations along the coding or control regions of sequences encoding PDE8.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding PDE8. These techniques are described both in Sambrook et al. (supra) and in Ausubel et al. (supra).

Genes encoding PDE8 can be turned off by transforming a cell or tissue with expression vectors which express high levels of a polynucleotide or fragment thereof which encodes PDE8. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding PDE8 (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding PDE8.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PDE8. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to. the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-,thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of PDE8, antibodies to PDE8, mimetics, agonists, antagonists, or inhibitors of PDE8. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of PDE8, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example PDE8 or fragments thereof, antibodies of PDE8, agonists, antagonists or inhibitors of PDE8, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind PDE8 may be used for the diagnosis of conditions or diseases characterized by expression of PDE8, or in assays to monitor patients being treated with PDE8, agonists, antagonists or inhibitors. The antibodies useful for diagnostic purposes may be prepared in the same manner as those described above for therapeutics. Diagnostic assays for PDE8 include methods which utilize the antibody and a label to detect PDE8 in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring PDE8 are known in the art and provide a basis for diagnosing altered or abnormal levels of PDE8 expression. Normal or standard values for PDE8 expression are established by combining body fluids or cell extracts taken from normal mammalian subjects, preferably human, with antibody to PDE8 under conditions suitable for complex formation. The amount of standard complex formation may be quantified by various methods, but preferably by photometric means. Quantities of PDE8 expressed in subject, control, and disease, samples from biopsied tissues are compared with the standard values. Deviation between standard and subject values establishes the parameters for diagnosing disease.

In another embodiment of the invention, the polynucleotides encoding PDE8 may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PDE8 may be correlated with disease. The diagnostic assay may be used to distinguish between absence, presence, and excess expression of PDE8, and to monitor regulation of PDE8 levels during therapeutic intervention.

In one aspect, hybridization with PCR probes which are capable of detecting polynucleotide sequences, including genomic sequences, encoding PDE8 or closely related molecules, may be used to identify nucleic acid sequences which encode PDE8. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding PDE8, alleles, or related sequences.

Probes may also be used for the detection of related sequences, and should preferably contain at least 50% of the nucleotides from any of the PDE8 encoding sequences. The hybridization probes of the subject invention may be DNA or RNA and derived from the nucleotide sequence of SEQ ID NO:2 or from genomic sequence including promoter, enhancer elements, and introns of the naturally occurring PDE8.

Means for producing specific hybridization probes for DNAs encoding PDE8 include the cloning of nucleic acid sequences encoding PDE8 or PDE8 derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding PDE8 may be used for the diagnosis of conditions or disorders which are associated with expression of PDE8. Examples of such conditions or disorders include cancers, such as adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; immune disorders, such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections; and trauma; and neuronal disorders, such as akathesia, Alzheimer's disease, amnesia, amyotrophic lateral sclerosis, bipolar disorder, catatonia, cerebral neoplasms, dementia, depression, Down's syndrome, tardive dyskinesia, dystonias, epilepsy, Huntington's disease, multiple sclerosis, neurofibromatosis, Parkinson's disease, paranoid psychoses, schizophrenia, and Tourette's disorder. The polynucleotide sequences encoding PDE8 may be used in Southern or northern analysis, dot blot, or other membrane-based technologies; in PCR technologies; or in dipstick, pin, ELISA assays or microarrays utilizing fluids or tissues from patient biopsies to detect altered PDE8 expression. Such qualitative or quantitative methods are well known in the art.

In a particular aspect, the nucleotide sequences encoding PDE8 may be useful in assays that detect activation or induction of various cancers, particularly those mentioned above. The nucleotide sequences encoding PDE8 may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding PDE8 in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of PDE8, a normal or standard profile for expression is established. This may be accomplished by combining body fluids or cell extracts taken from normal subjects, either animal or human, with a sequence, or a fragment thereof, which encodes PDE8, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PDE8 may involve the use of PCR. Such oligomers may be chemically synthesized, generated enzymatically, or produced in vitro. Oligomers will preferably consist of two nucleotide sequences, one with sense orientation (5'→3') and another with antisense (3'→5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of PDE8 include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of disease, to diagnose disease, and to develop and monitor the activities of therapeutic agents.

In one embodiment, the microarray is prepared and used according to the methods known in the art such as those described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619).

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably about 15 to 30 nucleotides in length, and most preferably about 20 to 25 nucleotides in length. For a certain type of microarray, it may be preferable to use oligonucleotides which are only 7 to 10 nucleotides in length. The microarray may contain oligonucleotides which cover the known 5' (or 3') sequence, or may contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from 2 to 1,000,000.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon or any other type of membrane, filter, chip, glass slide, or any other suitable solid support.

In one aspect, the oligonucleotides may be synthesized on the surface of the substrate by using a chemical coupling procedure and an ink jet application apparatus, such as that described in PCT application WO95/251116 (Baldeschweiler et al.). In another aspect, a "gridded" array analogous to a dot or slot blot HYBRIDOT apparatus, Life Technologies may be used to arrange and link cDNA fragments or oligonucleotides to the surface of a substrate using a vacuum system, thermal, UV, mechanical or chemical bonding procedures. In yet another aspect, an array may be produced by hand or by using available devices, materials, and machines (including Multichannel pipettors of robotic instrument; Brinkmann, Westbury, N.Y.) and may contain 8, 24, 96, 384, 1536 or 6144 oligonucleotides, or any other multiple from 2 to 1,000,000 which lends itself to the efficient use of conmmercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling Kits (Amersharn Pharmacia Biotech) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. A detection system may be used to measure the absence, presence, and amount of hybridization for all of the distinct sequences simultaneously. This data may be used for large scale correlation studies or functional analysis of the sequences, mutations, variants, or polymorphisms among samples (Heller, R. A. et al., (1997) Proc. Nati. Acad. Sci. 94:2150–55).

In another embodiment of the invention, the nucleic acid sequences which encode PDE8 may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding PDE8 on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, PDE8, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between PDE8 and the agent being tested, may be measured.

Another technique for drug screening which may be used provides for high throughput screening of compounds having suitable binding affinity to the protein of interest as described in published PCT application WO84/03564. In this method, as applied to PDE8 large numbers of different small test compounds are synthesized on a solid substrate, such as plastic pins or some other surface. The test compounds are reacted with PDE8, or fragments thereof, and washed. Bound PDE8 is then detected by methods well known in the art. Purified PDE8 can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PDE8 specifically compete with a test compound for binding PDE8. In this manner, the antibodies can be used to detect the presence of any peptide which shares one or more antigenic determinants with PDE8.

In additional embodiments, the nucleotide sequences which encode PDE8 may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

THP1PLB02

The THP1PLB02 cDNA library was constructed by reamplification of THP1PLB01. The THP1PLB01 cDNA library was made from activated human monocytes by Stratagene (Stratagene, La Jolla, Calif.). Poly(A+)RNA was purified from THP-1 cells which were cultured for 48 hr with 100 nm TPA and activated with 1 µg/ml LPS after 4 hr. cDNA synthesis was primed separately with both oligo d(T) and random hexamers. Synthetic adaptor oligonucleotides were ligated onto cDNA ends enabling insertion into UNIZAP vector system (Stratagene). After construction, the two libraries were combined into a single library by mixing equal numbers of bacteriophage.

The cDNA library was screened with either DNA probes or antibody probes and the PBLUESCRIPT phagemid (Stratagene) was excised in vivo. The custom-constructed library phage particles were transfected into E. coli host strain XL-I BLUE (Stratagene). Alternative unidirectional vectors include, but are not limited to, pcDNAI (Invitrogen, San Diego, Calif.) and pSHlox-1 (Novagen, Madison, Wis.).

LATRNOT01

The LATRNOT01 cDNA library was obtained from left ventricle tissue from a 51 year-old Caucasian female (Lot No. RU95-03-196, IIAM).

The tissue was flash frozen and ground in a mortar and pestle. The tissue was lysed immediately in buffer containing guanidinium isothiocyanate and spun through cesium chloride. The precipitate was treated by several phenol chloroform extractions and ethanol precipitation at pH 8. The polyadenylated mRNA was then isolated, treated with DNase, and purified using OLIGOTEX (Qiagen Inc., Chatsworth Calif.)

First strand cDNA synthesis was accomplished using an oligo d(T) primer/linker which also contained an XhoI restriction site. Second strand synthesis was performed using a is combination of DNA polymerase I, E. coli ligase, and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LAMBDAZAP vector system (Stratagene); and the vector which contained the PBLUESCRIPT phagemid (Stratagene) was transformed into E. coli host cells strain XL-IBLUEMRF (Stratagene).

II Isolation and Sequencing of cDNA Clones

THP1PLB02 and LATRNOT01

The phagemid forms of individual cDNA clones were obtained by the in vivo excision process, in which the host bacterial strain was coinfected with both the lambda library phage and an f1 helper phage. Polypeptides derived from both the library-containing phage and the helper phage nicked the lambda DNA, initiated new DNA synthesis from defined sequences on the lambda target DNA, and created a smaller, single stranded circular phagemid DNA molecule that included all DNA sequences of the PBLUESCRIPT plasmid and the cDNA insert.

The phagemid DNA was secreted from the cells, purified, and used to re-infect fresh host cells, where the double stranded phagemid DNA was produced. Because the phagemid carries the gene for β-lactamase, the newly-transformed bacteria were selected on a medium containing ampicillin.

The THP1PLB02 phagemid DNA was purified using the MAGIC MINIPREPS DNA purification system (Promega catalogue #A7100; Promega, Madison, Wis.). The LATRNOT01 plasmnid DNA was released from the cells and purified using the Miniprep Kit (Catalogue #77468; Advanced Genetic Technologies Corporation, Gaithersburg Md.). This kit consists of a 96 well block with reagents for 960 purifications. Alternatively, phagemid DNA was purified using the QIAWELL-8Plasmid, QIAWELL PLUS, and QIAWELL ULTRA DNA purification system (QIAGEN, Chatsworth, Calif.). The DNA was eluted from the purification resin already prepared for DNA sequencing and other analytical manipulations.

The cDNAs were sequenced by the method of Sanger F and A. R. Coulson (1975; J Mol. Biol. 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

THP1PLB02

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

LATRNOT01

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, which stands for Basic Local Alignment Search Tool (Altschul, S.F. (1993) J. Mol. Evol 36:290–300; Altschul, et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992, Protein Engineering 5:35–51), incorporated herein by reference, could have been used when dealing with primary sequence patterns and secondary structure gap penalties. The sequences disclosed in this application have lengths of at least 49 nucleotides, and no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam); and deduced amino acid sequences from the same clones were then searched against GenBank functional protein databases, mammalian (mamp), vertebrate (vrtp), and eukaryote (eukp) for homology.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Human multiple tissue northern blots (Clontech, Palo Alto, Calif.) were hybridized with a probe consisting of the 5' most 939 nucleotides of clone 156196. Probe DNA was labeled with $^{32}$P using the "Ready-To-Go" random prime labeling kit (Amersham Pharmacia Biotech) and washed to a stringency of 0.5×SSC, 65° C.

The highest levels of PDE8A were seen in testis, ovary, small intestine, and colon, but detectable levels were seen in heart, brain, placenta, lung, liver, skeletal muscle, kidney, pancreas, spleen, and prostate.

Computer techniques analogous to membrane based northern analysis were also performed using BLAST (Altschul (1993), supra; Altschul (1990), supra). The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding PDE8 occurs. Abundance and percent abundance are also reported. Abundance directly reflects the number of times a particular transcript is represented in a cDNA library, and percent abundance is abundance divided by the total number of sequences examined in the cDNA library.

V Extension of PDE8 Encoding Polynucleotides cDNA sequences containing 5' extensions of ESTs were extended by PCR amplification using human λgt10 testis or stomach cDNA libraries (Clontech Laboratories, Inc. Palo Alto, Calif.) and nested primers. For each reaction, 2.5×10$^7$ pfu were boiled for 5 minutes to release DNA. First round PCR (15 cycles) was performed with a PDE8A specific primer (8A specific-outer: 5'-GAAGCACATCAGCAGAAT-3', SEQ ID NO:10) and either a λgt10 forward (5'-TCGCTTAGTTTTACCGTTT-3', SEQ ID NO:11 or a λgt10 reverse (5'-TATCGCCTCCATCAACAAACTT-3', SEQ ID NO:12) primer. An aliquot, 1/50 of the reaction mixture, was used as a template for a second round of amplification (30 cycles) with a PDE8A specific primer (8A specific-inner: 5'-TTGTGGTAGGGATTGGAG-3', SEQ ID NO:13) with either a nested λgt10 forward (5'-AGCAAGTTCAGCCTGGTTAAG-3', SEQ ID NO:14) or λgt10 reverse (5'-CTTATGAGTATTTCTTCCAGGGTA-3', SEQ ID NO:15) primer. Southern analysis of the PCR products used an internal PDE8A hybridization probe (5'-ATCATGGTTACAAATTATCGAAGCCAATTA-3', SEQ ID NO:16). Positive bands were subcloned and sequenced. All sequences subsequently incorporated into the extended PDE8A sequence were verified by sequencing multiple independent PCR amplifications from the cDNA library DNA using unique primers, or by independent amplification from mRNA.

VI Labeling and Use of Individual Hybridization Probes

Hybridization probes derived from polynucleotide sequences of the invention are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 Software (National Biosciences), labeled by combining 50 pmol of each oligomer and 250 μCi of [γ-$^{32}$P] adenosine triphosphate (Amersham Pharmacia Biotech) and T4 polynucleotide kinase (DuPont NEN, Boston, Mass.). The labeled oligonucleotides are substantially purified with SEPHADEX G-25 superfine resin column (Amersham Pharmacia Biotech). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Eastman) is exposed to the blots in a Phosphoimager cassette (Molecular Dynamics, Sunnyvale, Calif.) for several hours, hybridization patterns are compared visually.

VII Microarrays

To produce oligonucleotides for a microarray, one of the nucleotide sequences of the present invention are examined using a computer algorithm which starts at the 3' end of the nucleotide sequence. The algorithm identified oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20 mers are synthesized and arranged on the surface of the silicon chip using a light-directed chemical process, such as that discussed in Chee, supra.

In the alternative, a chemical coupling procedure and an ink jet device are used to synthesize oligomers on the surface of a substrate (cf. Baldeschweiler, supra). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. A typical array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned image is examined to determine degree of complementarity and the relative abundance/expression level of each oligonucleotide sequence in the microarray.

VIII Complementary Polynucleotides

Sequences complementary to the PDE8-encoding sequence, or any part thereof, are used to decrease or inhibit expression of naturally occurring PDE8. Although use of oligonucleotides comprising from about 15 to about 30 base-pairs is described, essentially the same procedure is used with smaller or larger sequence fragments. Appropriate oligonucleotides are designed using Oligo 4.06 software (National Biosciences)and the coding sequence of PDE8. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PDE8-encoding transcript.

IX Expression of PDE8

A 1.6 kb region of PDE8A(E) (the C-terminal 545 amino acids) was amplified and cloned into the baculovirus transfer vector pFASTBAC (Life Technologies, Inc., Gaithersburg, Md.), which had been modified to include a 5° FLAG tag. Recombinant virus stocks were prepared according to the manufacturer's protocol. Sf9 cells were cultured in Sf900 II Sfm serum free media (Life Technologies Inc.) at 27° C. For expression, $1 \times 10^8$ Sf9 cells were infected at a multiplicity of infection of 5 in a final volume of 50 mls. At three days post-infection, the cells were harvested, and enzyme-containing lysates were prepared as detailed below. To monitor expression, 1 ml each of mock-infected and PDE8A (E) infected cell lysate was electrophoresed in a polyacrylamide gel and either silver-stained by standard methods or transferred to nitrocellulose and assayed using western analysis and an anti-FLAG antibody (M2, Scientific Imaging System, Eastman Kodak, New Haven, Conn.) at a concentration of 2 mg/ml. The secondary antibody was an alkaline phosphatase conjugated Anti-Mouse IgG (Boehringer Mannheim, Indianapolis, Ind.) and the blot was visualized with a "BCIP/NBT phosphatase substrate system" (Kirkegaard & Perry Laboratories, Gaithersburg, Md.) according to the manufactures protocol.

PDE8A(E) to be used for assay was prepared from transfected Sf9 cells. Cells were harvested by centrifugation, resuspended in homogenization buffer (20 mM Tris-HCl, 2 mM benzamidine, 1mM EDTA, 0.25 M sucrose, 100 uM PMSF, pH 7.5 ) at $1 \times 10^7$ cells/ml, and disrupted using a Branson sonicating probe (3×10 second pulses). Cellular debris was removed by centrifugation at 14,000×g for 10 minutes. The supernatant was stored at −70° C.

X Demonstration of PDE8 Activity

PDE activity was assayed by measuring the conversion of $^3$H-cAMP to $^3$H-adenosine in the presence of PDE8A(E) and 5' nucleotidase. A one-step assay was run using a 100 uL assay containing 50 mM Tris-HCl pH 7.5, 10 mM $MgCl^2$, 0.1 unit 5' nucleotidase (from *Crotalus atrox* venom), 0.0062–0.1 uM $^3$H-cAMP, and various concentrations of cAMP (0.0062–3 mM). The reaction was started by the addition of 25 ul of diluted enzyme supernatant. Reactions were run directly in mini Poly-Q scintillation vials (Beckman Instruments Inc., Fullerton Calif.). Assays were incubated at 37° C. for a time period that would give less than 15% cAMP hydrolysis to avoid non-linearity associated with product inhibition. The reaction was stopped by the addition of 1 ml of Dowex AG1×8 (Cl form) resin (1:3 slurry). Three ml of scintillation fluid were added, and the vials were mixed. The resin in the vials was allowed to settle for 1 hr before counting. Soluble radioactivity associated with $^3$H-adenosine was quantitated using a Beta scintillation counter. The amount of radioactivity recovered is proportional to the activity of PDE8 in the reaction. For inhibitor studies (FIG. 8), all reactions contained 1% DMSO, 50 nM cAMP, and the indicated inhibitor concentrations. The control vial contained all reagents minus the enzyme aliquot.

XI Production of PDE8 Specific Antibodies

PDE8 that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using LASERGENE software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring PDE8 Using Specific Antibodies

Naturally occurring or recombinant PDE8 is substantially purified by immunoaffinity chromatography using antibodies specific for PDE8. An immunoaffinity column is constructed by covalently coupling PDE8 antibody to an activated chromatographic resin, such as CNBr-activated SE(Amersham Pharmacia Biotech). After the coupling, the resin is blocked and washed according to the manufacturer's instructions.

Media containing PDE8 is passed over the immunoaffinity column, and the column is washed under conditions that allow the preferential absorbance of PDE8 (e.g. high ionic strength buffers in the presence of detergent). The column is eluted under conditions that disrupt antibody/PDE8 binding (eg, a buffer of pH 2–3 or a high concentration of a chaotrope, such as urea or thiocyanate ion), and PDE8 is collected.

XIII Identification of Molecules Which Interact with PDE8

PDE8 or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled PDE8, washed and any wells with labeled PDE8 complex are assayed. Data obtained using different concentrations of PDE8 are used to calculate values for the number, affinity, and association of PDE8 with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. A substantially purified polypeptide, wherein the polypeptide is a cyclic nucleotide phosphodiesterase (PDE8) comprising an amino acid sequence selected from SEQ ID NO:5 and SEQ ID NO:7.

2. A substantially purified polypeptide consisting of the amino acid sequence of SEQ ID NO:5 or SEQ ID NO:7 or a fragment thereof of at least 8 consecutive amino acids.

3. The polypeptide of claim 2 wherein the polypeptide consists of a sequence selected from SEQ ID NO:1 and SEQ ID NO:3.

4. A method for using a polypeptide to screen a library of molecules or compounds to identify at least one molecule or compound which specifically binds the polypeptide, the method comprising:

(a) combining the purified polypeptide of claim 2 with the library of molecules or compounds under conditions to allow specific binding, and (b) detecting specific binding thereby identifying a molecule or compound which specifically binds the purified polypeptide.

5. A method of using a polypeptide to purify a molecule or compound which specifically binds the polypeptide from a sample, the method comprising:

(a) combining the purified polypeptide of claim 2 with a sample under conditions to allow the specific binding, thereby producing polypeptide bound to a molecule or compound;

(b) recovering the bound polypeptide; and (c) separating the polypeptide from the molecule or compound, thereby obtaining purified molecule or compound.

6. The method of claim 4 wherein the library is selected from peptides, antibodies, inhibitors, drug compounds, and pharmaceutical agents.

* * * * *